(12) United States Patent
Hill et al.

(10) Patent No.: US 6,576,596 B1
(45) Date of Patent: Jun. 10, 2003

(54) SUBSTITUTED 2-BENZOYL-CYCLOHEXAN-1,3-DIONES WITH HERBICIDAL EFFECT

(75) Inventors: Regina Luise Hill, Speyer (DE); Uwe Kardorff, Mannheim (DE); Michael Rack, Heidelberg (DE); Ernst Baumann, Dudenhofen (DE); Wolfgang von Deyn, Neustadt (DE); Stefan Engel, Idstein (DE); Guido Mayer, Neustadt (DE); Martina Otten, Ludwigshafen (DE); Joachim Rheinheimer, Ludwigshafen (DE); Matthias Witschel, Ludwigshafen (DE); Ulf Misslitz, Neustadt (DE); Helmut Walter, Obrigheim (DE); Karl-Otto Westphalen, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/331,639

(22) PCT Filed: Dec. 19, 1997

(86) PCT No.: PCT/EP97/07214

§ 371 (c)(1),
(2), (4) Date: Jun. 23, 1999

(87) PCT Pub. No.: WO98/29384

PCT Pub. Date: Sep. 7, 1998

(30) Foreign Application Priority Data

Jan. 3, 1997 (DE) .......................... 197 00 019

(51) Int. Cl.$^7$ ........................ A01N 35/10; A01N 37/34; A01N 43/32; A01N 47/40
(52) U.S. Cl. ..................... 504/344; 504/288; 504/290; 504/292; 504/293; 504/310; 504/343; 504/348; 504/349; 549/14; 549/22; 549/372; 549/425; 558/422; 564/251; 564/300
(58) Field of Search ................. 504/349, 344, 504/348, 238, 290, 292, 293, 310, 343; 564/300, 251; 549/14, 22, 372, 425; 558/422

(56) References Cited

U.S. PATENT DOCUMENTS

| | | | |
|---|---|---|---|
| 3,872,113 A | 3/1975 | Fliendner, Jr. ......... 260/240 G |
| 4,647,698 A | * 3/1987 | Henrick ....................... 564/256 |
| 4,943,310 A | 7/1990 | Angermann et al. ........... 71/38 |
| 5,167,696 A | * 12/1992 | Chrystal et al. ............... 71/106 |
| 6,150,304 A | * 11/2000 | Fischer et al. .............. 504/309 |

FOREIGN PATENT DOCUMENTS

| | | |
|---|---|---|
| CA | 2204667 | 3/1996 |
| EP | 137 963 | 4/1985 |
| EP | 278 742 | 8/1988 |
| EP | 298 680 | 1/1989 |
| WO | 90/05712 | 5/1990 |
| WO | 97/46530 | 12/1997 |

OTHER PUBLICATIONS

Database Crossfire, Beilstein, XP002063835.
Shah et al. "γ-Substitution on the Resorcinol Nucleus Synthesis of γ-Resorcylaldehyde" J. Chem. Soc. (1938) pp. 1828–1832.

* cited by examiner

Primary Examiner—Peter O'Sullivan
(74) Attorney, Agent, or Firm—Keil & Weinkauf

(57) ABSTRACT

The invention relates to 2-benzoylcyclohexane-1,3-diones of the formula I where
$R^1$, $R^2$ are each hydrogen, nitro, halogen, cyano, thiocyanato, alkyl, haloalkyl, alkoxyalkyl, alkenyl, alkynyl, —$OR^5$, —$OCOR^6$, —$OSO_2R^6$, —SH, —S(O)$_nR^7$, —$SO_2OR^5$, —$SO_2NR^5R^8$, —$NR^8SO_2R^6$ or —$NR^8COR^6$;
$R^3$ is hydrogen, cyano, alkyl, haloalkyl, —$OR^7$, —$SR^7$ or —$NR^7R^{10}$;
$R^4$ is hydrogen, substituted or unsubstituted alkyl, cycloalkyl, alkenyl, cycloalkenyl, alkynyl, —$COR^9$, —$CO_2R^9$, —$COSR^9$ or —$CONR^8R^9$;
X is oxygen or $NR^8$;
n is 0, 1 or 2;
$R^5$ is hydrogen, alkyl, haloalkyl, alkoxyalkyl, alkenyl or alkynyl;
$R^6$ is alkyl or haloalkyl;
$R^7$ is alkyl, haloalkyl, alkoxyalkyl, alkenyl or alkynyl;
$R^8$ is hydrogen or alkyl;
$R^9$ is alkyl, alkenyl, alkynyl, phenyl or benzyl;
$R^{10}$ is alkyl, haloalkyl, alkenyl or alkynyl;
Q is a cyclohexane-1,3-dione ring with or without substitution attached in position 2;
and agriculturally useful salts thereof;
to processes and intermediates for preparing the compounds of the formula I; to compositions comprising them; and to the use of these derivatives or compositions comprising them for controlling undesirable plants.

10 Claims, No Drawings

SUBSTITUTED 2-BENZOYL-CYCLOHEXAN-1,3-DIONES WITH HERBICIDAL EFFECT

This application is a 370 of PCT/EP97/07214 filed Dec. 19, 1997.

The present invention relates to substituted 2-benzoyl-cyclohexane-1,3-diones of the formula I

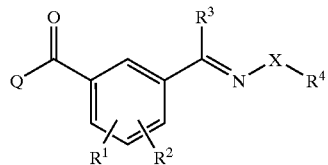

where:
R$^1$ and R$^2$ are are each hydrogen, nitro, halogen, cyano, thiocyanato, C$_1$–C$_6$-alkyl, C$_1$–C$_6$-haloalkyl, C$_1$–C$_6$-alkoxy-C$_1$–C$_6$-alkyl, C$_2$–C$_6$-alkenyl, C$_2$–C$_6$-alkynyl, —OR$^5$, —OCOR$^6$, —OSO$_2$R$^6$, —SH, —S(O)$_n$R$^7$, —SO$_2$OR$^5$, —SO$_2$NR$^5$R$^8$, —NR$^8$SO$_2$R$^6$ or —NR$^8$COR$^6$;
R$^3$ is hydrogen, cyano, C$_1$–C$_6$-alkyl, C$_1$–C$_6$-haloalkyl, —OR$^7$, —SR$^7$ or —NR$^7$R$^{10}$;
R$^4$ is hydrogen, C$_1$–C$_6$-alkyl, C$_3$–C$_6$-cycloalkyl, C$_3$–C$_6$-alkenyl, C$_4$–C$_6$-cycloalkenyl, C$_3$–C$_6$-alkynyl, —COR$^9$, —CO$_2$R$^9$, —COSR$^9$ or —CONR$^8$R$^9$, where the alkyl, cycloalkyl, alkenyl, cycloalkenyl and alkynyl radicals mentioned and R$^9$ of the radicals —COR$^9$, —CO$_2$R$^9$, —COSR$^9$ and —CONR$^8$R$^9$ may be partially or fully halogenated and/or carry one to three of the following groups:
hydroxyl, mercapto, amino, cyano, R$^{10}$, —OR$^{10}$, —SR$^{10}$, —NR$^8$R$^{10}$, =NOR$^{10}$, —OCOR$^{10}$, —SCOR$^{10}$, —NR$^8$COR$^{10}$, —CO$_2$R$^{10}$, —COSR$^{10}$, —CONR$^8$R$^{10}$, C$_1$–C$_4$-alkyliminooxy, C$_1$–C$_4$-alkoxyamino, C$_1$–C$_4$-alkylcarbonyl, C$_1$–C$_4$-alkoxy-C$_2$–C$_6$-alkoxycarbonyl, C$_1$–C$_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;
X is oxygen or NR$^8$:
n is 0, 1 or 2;
R$^5$ is hydrogen, C$_1$–C$_6$-alkyl, C$_1$–C$_6$-haloalkyl, C$_1$–C$_6$-alkoxy-C$_2$–C$_6$-alkyl, C$_3$–C$_6$-alkenyl or C$_3$–C$_6$-alkynyl;
R$^6$ is C$_1$–C$_6$-alkyl or C$_1$–C$_6$-haloalkyl;
R$^7$ is C$_1$–C$_6$-alkyl, C$_1$–C$_6$-haloalkyl, C$_1$–C$_6$-alkoxy-C$_2$–C$_6$-alkyl, C$_3$–C$_6$-alkenyl or C$_3$–C$_6$-alkynyl;
R$^8$ is hydrogen or C$_1$–C$_6$-alkyl;
R$^9$ is C$_1$–C$_6$-alkyl, C$_3$–C$_6$-alkenyl, C$_3$–C$_6$-alkynyl, phenyl or benzyl;
R$^{10}$ is C$_1$–C$_6$-alkyl, C$_1$–C$_6$-haloalkyl, C$_3$–C$_6$-alkenyl or C$_3$–C$_6$-alkynyl;
Q is a cyclohexane-1,3-dione ring attached in position 2 with or without substitution;
and agriculturally useful salts thereof.

The invention additionally relates to processes and intermediates for preparing compounds of the formula I, to compositions comprising them, and to the use of the compounds of the formula I or of compositions comprising them for controlling harmful plants.

2-Benzoylcyclohexane-1,3-diones are known from the literature, for example from EP-A 278 742, EP-A 298 680, EP-A 320 864 and WO 96/14285.

However, the herbicidal properties of these prior art compounds and their compatibility with crop plants are not entirely satisfactory.

It is an object of the present invention to provide novel, in particular herbicidally active, compounds having improved properties.

We have found that this object is achieved by the 2-benzoyl-cyclohexane-1,3-diones of the formula I and their herbicidal action.

Furthermore, the invention provides herbicidal compositions comprising the compounds I and having a very good herbicidal activity. Additionally, the invention provides processes for preparing these compositions and methods for controlling undesirable vegetation using the compounds I.

The present invention also provides stereoisomers of the compounds of the formula I. Pure stereoisomers and also mixtures thereof are included.

The compounds of the formula I contain a carbon-nitrogen double bond and are therefore present as E isomers or Z isomers or as E/Z isomer mixtures. Furthermore, the compounds of the formula I may contain further carbon-carbon or carbon-nitrogen double bonds. The invention provides the pure geometric isomers and also mixtures thereof.

Depending on the substitution pattern, the compounds of the formula I may contain one or more chiral centers and, if this is the case, are present as mixtures of enantiomers or diastereomers. The invention provides the pure enantiomers or diastereomers and also mixtures thereof.

The compounds of the formula I may also be present in the form of their agriculturally useful salts, the kind of salt generally not being important. The salts of those cations or the acid additon salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and ammonium, where, if desired, one to four hydrogen atoms may be replaced by C$_1$–C$_4$-alkyl or hydroxyl-C$_1$–C$_4$-alkyl and/or one phenyl or benzyl, preferably diisopropylammonium, tetramethylammonium, tetrabutylammonium, trimethylbenzylammonium, furthermore phosphonium ions, sulfonium ions, preferably tri (C$_1$–C$_4$-alkyl)sulfonium and sulfoxonium ions, preferably tri(C$_1$–C$_4$-alkyl)sulfoxonium.

Anions of usable acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of C$_1$–C$_4$-alkanoic acids, preferably formate, acetate, propionate and butyrate.

Emphasis is given to compounds of the formula I according to the invention where the variable Q is a cyclohexane-1,3-dione ring of the formula II linked in position 2

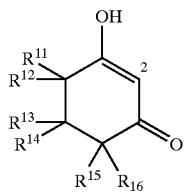

where II also represents the tautomeric formulae II' and II",

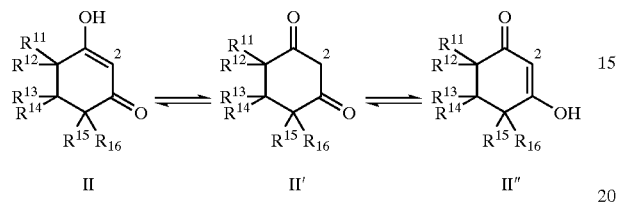

where $R^{11}$, $R^{12}$, $R^{14}$ and $R^{16}$ are each hydrogen or $C_1$–$C_4$-alkyl;

$R^{13}$ is hydrogen, $C_1$–$C_4$-alkyl or $C_3$–$C_4$-cycloalkyl, where the last two groups may carry one to three of the following substituents: halogen, $C_1$–$C_4$-alkylthio or $C_1$–$C_4$-alkoxy; or is tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl; 1,3-dioxan-2-yl, 1,3-oxathiolan-2-yl, 1,3-oxathian-2-yl, 1,3-dithiolan-2-yl or 1,3-dithian-2-yl, where the last 6 radicals mentioned may be substituted by one to three $C_1$–$C_4$-alkyl radicals;

$R^{15}$ is hydrogen, $C_1$–$C_4$-alkyl or $C_1$–$C_6$-alkoxycarbonyl; or $R^{13}$ and $R^{16}$ together form a π-bond or a three- to six-membered carbocyclic ring; or the $CR^{13}R^{14}$ unit is replaced by C=O.

Emphasis is also given to compounds of the formula I according to the invention where $R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$ where the alkyl, cycloalkyl, alkenyl-, cycloalkenyl and alkynyl radicals mentioned and $R^9$ of the radicals —$COR^9$, —$CO_2R^9$, —$COSR^9$ and —$CONR^8R^9$ may be partially or fully halogenated and/or carry one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be partially or fully halogenated and/or carry one to three radicals from the following group:

nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl.

The organic moieties mentioned for the substituents $R^1$–$R^{16}$ or as radicals on phenyl, hetaryl and heterocylyl rings represent collective terms for lists of the individual group members. All hydrocarbon chains, ie. all alkyl, haloalkyl, cycloalkyl, alkoxyalkyl, alkoxy, haloalkoxy, alkyliminooxy, alkoxyamino, alkylthio, alkylsulfonyl, alkylcarbonyl, alkoxycarbonyl, alkoxyalkoxycarbonyl, alkenyl, cycloalkenyl and alkynyl moieties, may be straight-chain or branched. Unless stated otherwise, preference is given to halogenated substituents carrying one to five identical or different halogens. Halogen is in each case fluorine, chlorine, bromine or iodine.

Furthermore, the following moities represent, for example:

$C_2$–$C_4$-alkyl: ethyl, propyl, 1-methylethyl, butyl, 1-methylpropyl, 2-methylpropyl and 1,1-dimethylethyl;

$C_1$–$C_4$-alkyl and the alkyl moieties of $C_1$–$C_4$-alkylcarbonyl: $C_2$–$C_4$-alkyl as mentioned above, and methyl;

$C_2$–$C_6$-alkyl, and the alkyl moieties of $C_1$–$C_6$-alkoxy-$C_2$–$C_6$-alkyl: $C_2$–$C_4$-alkyl as mentioned above, and pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_6$-alkyl and the alkyl moieties of $C_1$–$C_6$-alkoxy-$C_1$–$C_6$-alkyl: $C_2$–$C_6$-alkyl as mentioned above, and methyl;

$C_1$–$C_4$-haloalkyl: a $C_1$–$C_4$-alkyl radical as mentioned above which is partially or fully substituted by fluorine, chlorine, bromine and/or iodine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl: $C_1$–$C_4$-haloalkyl as mentioned above, and 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy and the alkoxy moieties of $C_1$–$C_4$-alkoxyamino, $C_1$–$C_4$-alkoxy-$C_2$–$C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties of $C_1$–$C_6$-alkoxy-$C_1$–$C_6$-alkyl, $C_1$–$C_4$-alkoxy-$C_2$–$C_6$-alkoxycarbonyl and $C_1$–$C_6$-alkoxycarbonyl: $C_1$–$C_4$-alkoxy as mentioned above, and pentoxy, 1-methylbutoxy, 2-methylbutoxy, 3-methylbutoxy, 1,1- dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully subsstituted by fluorine, chlorine, bromine and/or iodine, ie. for example fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chlor-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylthio: methylthio, ethylthio, propylthio, 1-methylethylthio, butylthio, 1-methylpropylthio, 2-methylpropylthio and 1,1-dimethylethylthio;

$C_1$–$C_4$-alkylsulfonyl ($C_1$–$C_4$-alkyl-S(=O)$_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_4$-alkyliminooxy: methyliminooxy, ethyliminooxy, 1-propyliminooxy, 2-propyliminooxy, 1-butyliminooxy and 2-butyliminooxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl: $C_3$–$C_6$-alkenyl as mentioned above, and ethenyl;

$C_3$–$C_6$-alkynyl: prop-1-yn-1-yl, prop-2-yn-1-yl, but-1-yn-1-yl, but-1-yn-3-yl, but-1-yn-4-yl but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: $C_3$–$C_6$-alkynyl as mentioned above, and ethynyl:

$C_3$–$C_6$-cycloalkyl: cyclopropyl, cyclobutyl, cyclopentyl and cyclohexyl;

$C_4$–$C_6$-cycloalkenyl: cyclobuten-1-yl, cyclobuten-3-yl, cyclopenten-1-yl, cyclopenten-3-yl, cyclopenten-4-yl, cyclohexen-1-yl, cyclohexen-3-yl and cyclohexen-4-yl;

heterocyclyl and the heroclyl [sic] radicals in heterocyclyloxy: three- to seven-membered saturated or partially unsaturated mono- or polycyclic heterocycles containing one to three hetero atoms selected from a group consisting of oxygen, nitrogen and sulfur, such as oxiranyl, oxetan-3-yl, thietan-3-yl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5- dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dioxan-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dithiolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, hetaryl and the hetaryl radicals in hetaryloxy:
aromatic mono- or polycyclic radicals which, in addition to carbon ring members, may contain one to four nitrogen atoms or one to three nitrogen atoms and one oxygen or one sulfur atom or one oxygen or one sulfur atom, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and the corresponding benzo-fused derivatives.

All phenyl and hetaryl rings are preferably unsubstituted or carry one to three halogens and/or one or two radicals from the following group: nitro, cyano, methyl, trifluoromethyl, methoxy, trifluoromethoxy or methoxycarbonyl.

Preferred with a view to the use of the compounds of the formula I according to the invention as herbicides are those compounds where the variables have the following meanings, in each case either on their own or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;

particularly preferably nitro, halogen such as, for example, fluorine, chlorine or bromine, $C_1$–$C_6$-haloalkyl, —$OR^5$ or —$SO_2R^7$ such as, for example, methylsulfonyl, ethylsulfonyl or difluoromethylsulfonyl; especially preferably nitro, fluorine, chlorine, bromine, trifluoromethyl, methoxy, ethoxy, methylsulfonyl, ethylsulfonyl or difluoromethylsulfonyl;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;

particularly preferably hydrogen, nitro, halogen such as, for example, fluorine, chlorine or bromine, $C_1$–$C_6$-alkyl such as, for example, methyl or ethyl, $C_1$–$C_6$-haloalkyl, —$OR^5$ or —$SO_2R^7$ such as, for example, methylsulfonyl, ethylsulfonyl or difluoromethylsulfonyl;

especially preferably nitro, fluorine, chlorine, bromine, methyl, ethyl, trifluoromethyl, methoxy, ethoxy, methylsulfonyl, ethylsulfonyl or difluoromethylsulfonyl;

$R^3$ is hydrogen, cyano, $C_1$–$C_6$-alkyl, $C_1$–$C_6$-haloalkyl or —$OR^7$;

$R^4$ is hydrogen, $C_1$–$C_6$-alkyl, $C_3$–$C_6$-cycloalkyl, $C_3$–$C_6$-alkenyl or $C_3$–$C_6$-alkynyl, where the last 4 substituents mentioned may be partially or fully halogenated and/or carry one to three of the following groups: hydroxyl, mercapto, amino, cyano, —$OR^{10}$, =$NOR^{10}$, —$OCOR^{10}$, —$CO_2R^{10}$, —$COSR^{10}$, —$CONR^8R^{10}$, $C_1$–$C_4$-alkyliminooxy, $C_1$–$C_4$-alkylcarbonyl, $C_1$–$C_4$-alkoxy-$C_2$–$C_6$-alkoxycarbonyl, heterocyclyl, heterocyclyloxy, phenyl, benzyl, hetaryl, phenoxy, benzyloxy or hetaryloxy, where the last eight radicals mentioned may in turn be partially or fully halogenated and/or carry one to three radicals from the following group:

nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

particularly preferably $C_1$–$C_6$-alkyl, $C_3$–$C_6$-cycloalkyl, $C_3$–$C_6$-alkenyl or $C_3$–$C_6$-alkynyl, where the last 4 substituents mentioned may be partially or fully halogenated and/or carry one to three of the following groups: hydroxyl, mercapto, amino, cyano, —$OR^{10}$, =$NOR^{10}$, —$OCOR^{10}$, —$CO_2R^{10}$, —$COSR^{10}$, —$CONR^8R^{10}$, $C_1$–$C_4$-alkyliminooxy, $C_1$–$C_4$-alkylcarbonyl, $C_1$–$C_4$-alkoxy-$C_2$–$C_6$-alkoxycarbonyl, heterocyclyl, heterocyclyloxy, phenyl, benzyl, hetaryl, phenoxy, benzyloxy or hetaryloxy, where the last eight radicals mentioned may in turn be partially or fully halogenated and/or carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

X is oxygen or NH;
n is 0 or 2
$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
particularly preferably methyl, ethyl, trifluoromethyl, difluoromethyl, methoxyethyl, allyl or propargyl;
$R^7$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
particularly preferably methyl, ethyl, trifluoromethyl, difluoromethyl, methoxyethyl, allyl or propargyl;

$R^8$ is hydrogen or $C_1$–$C_6$-alkyl;
$R^{10}$ is $C_1$–$C_6$-alkyl, $C_1$–$C_6$-haloalkyl, $C_3$–$C_6$-alkenyl or $C_3$–$C_6$-alkynyl;
$R^{11}$, $R^{12}$, $R^{14}$ and $R^{16}$ are each hydrogen or $C_1$–$C_4$-alkyl; particularly preferably hydrogen, methyl or ethyl;
$R^{13}$ is hydrogen, $C_1$–$C_4$-alkyl, $C_3$–$C_4$-cycloalkyl, where the last two groups may carry one to three of the following substituents: halogen, $C_1$–$C_4$-alkoxy or $C_1$–$C_4$-alkylthio; tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithian-2-yl or 1,3-dithiolan-2-yl, where the last six groups mentioned may in each case carry one to three $C_1$–$C_4$-alkyl radicals;
particularly preferably hydrogen, methyl, ethyl, cyclopropyl, di(methoxy)methyl, di(ethoxy)methyl, 2-ethylthiopropyl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 5,5-dimethyl-1,3-dioxan-2-yl, 1,3-oxathiolan-2-yl, 1,3-oxathian-2-yl, 1,3-dithiolan-2-yl, 5,5-dimethyl-1,3-dithian-2-yl or 1-methylthiocyclopropyl;
$R^{15}$ is hydrogen, $C_1$–$C_4$-alkyl or $C_1$–$C_4$-alkoxycarbonyl; particularly preferably hydrogen, methyl or methoxycarbonyl.

It may also be advantageous for $R^{13}$ and $R^{16}$ to form a π-bond, thus forming a double bond system.

The $CR^{13}R^{14}$ unit may also be advantageously replaced by C=O.

Particular preference is given to compounds of the formula Ia (≙ I where $R^1$ is attached in position 4 of the phenyl ring and $R^2$ is attached in position 2 of the phenyl ring).

Ia

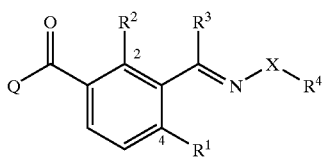

Very particular preference is given to the compounds of the formula Ia in which $R^1$ to $R^3$, Q and X are as defined above and $R^4$ is hydrogen, $C_1$–$C_6$-alkyl, $C_3$–$C_6$-cycloalkyl, $C_3$–$C_6$-alkenyl or $C_3$–$C_6$-alkynyl, where the last 4 substituents may be partially or fully halogenated and/or carry one to three of the following groups: hydroxyl, mercapto, amino, cyano, —$OR^{10}$, =$NOR^{10}$, —$OCOR^{10}$, —$CO_2R^{10}$, —$COSR^{10}$, —$CONR^8R^{10}$, $C_1$–$C_4$-alkyliminooxy, $C_1$–$C_4$-alkylcarbonyl, $C_1$–$C_4$-alkoxy-$C_2$–$C_6$-alkoxycarbonyl, heterocyclyl, heterocyclyloxy, phenyl, benzyl, hetaryl, phenoxy, benzyloxy or hetaryloxy, where the last eight radicals mentioned may in turn be partially or fully halogenated and/or carry one to three radicals from the following group:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl.

Most particular preference is given to the compounds Ia1 (≙ I where $R^1$=Cl, $R^{11}$, $R^{12}$, $R^{13}$, $R^{14}$, $R^{15}$, $R^{16}$=H, $R^1$ being attached in position 4 of the phenyl ring and $R^2$ being attached in position 2 of the phenyl ring), in particular the compounds of Table 1.

TABLE 1

Ia1

| No. | $R^2$ | $R^3$ | $R^4$ | X |
|---|---|---|---|---|
| Ia1.001 | Cl | H | $CH_3$ | O |
| Ia1.002 | Cl | H | $C_2H_5$ | O |
| Ia1.003 | Cl | H | $CH_2$—C≡CH | O |
| Ia1.004 | Cl | $CH_3$ | $CH_3$ | O |
| Ia1.005 | Cl | $CH_3$ | $C_2H_5$ | O |
| Ia1.006 | Cl | $CH_3$ | $CH_2$—C≡CH | O |
| Ia1.007 | Cl | $C_2H_5$ | $CH_3$ | O |
| Ia1.008 | Cl | $C_2H_5$ | $C_2H_5$ | O |
| Ia1.009 | Cl | $C_2H_5$ | $CH_2$—C≡CH | O |
| Ia1.010 | Cl | $OCH_3$ | $CH_3$ | O |
| Ia1.011 | Cl | $OCH_3$ | $C_2H_5$ | O |
| Ia1.012 | Cl | $OCH_3$ | $CH_2$—C≡CH | O |
| Ia1.013 | Cl | $OC_2H_5$ | $CH_3$ | O |
| Ia1.014 | Cl | $OC_2H_5$ | $C_2H_5$ | O |
| Ia1.015 | Cl | $OC_2H_5$ | $CH_2$—C≡CH | O |
| Ia1.016 | Cl | H | $CH_3$ | NH |
| Ia1.017 | Cl | H | $C_2H_5$ | NH |
| Ia1.018 | Cl | H | $CH_2$—C≡CH | NH |
| Ia1.019 | Cl | $CH_3$ | $CH_3$ | NH |
| Ia1.020 | Cl | $CH_3$ | $C_2H_5$ | NH |
| Ia1.021 | Cl | $CH_3$ | $CH_2$—C≡CH | NH |
| Ia1.022 | Cl | $C_2H_5$ | $CH_3$ | NH |
| Ia1.023 | Cl | $C_2H_5$ | $C_2H_5$ | NH |
| Ia1.024 | Cl | $C_2H_5$ | $CH_2$—C≡CH | NH |
| Ia1.025 | Cl | $OCH_3$ | $CH_3$ | NH |
| Ia1.026 | Cl | $OCH_3$ | $C_2H_5$ | NH |
| Ia1.027 | Cl | $OCH_3$ | $CH_2$—C≡CH | NH |
| Ia1.028 | Cl | $OC_2H_5$ | $CH_3$ | NH |
| Ia1.029 | Cl | $OC_2H_5$ | $C_2H_5$ | NH |
| Ia1.030 | Cl | $OC_2H_5$ | $CH_2$—C≡CH | NH |
| Ia1.031 | $CH_3$ | H | $CH_3$ | O |
| Ia1.032 | $CH_3$ | H | $C_2H_5$ | O |
| Ia1.033 | $CH_3$ | H | $CH_2$—C≡CH | O |
| Ia1.034 | $CH_3$ | $CH_3$ | $CH_3$ | O |
| Ia1.035 | $CH_3$ | $CH_3$ | $C_2H_5$ | O |
| Ia1.036 | $CH_3$ | $CH_3$ | $CH_2$—C≡CH | O |
| Ia1.037 | $CH_3$ | $C_2H_5$ | $CH_3$ | O |
| Ia1.038 | $CH_3$ | $C_2H_5$ | $C_2H_5$ | O |
| Ia1.039 | $CH_3$ | $C_2H_5$ | $CH_2$—C≡CH | O |
| Ia1.040 | $CH_3$ | $OCH_3$ | $CH_3$ | O |
| Ia1.041 | $CH_3$ | $OCH_3$ | $C_2H_5$ | O |
| Ia1.042 | $CH_3$ | $OCH_3$ | $CH_2$—C≡CH | O |
| Ia1.043 | $CH_3$ | $OC_2H_5$ | $CH_3$ | O |
| Ia1.044 | $CH_3$ | $OC_2H_5$ | $C_2H_5$ | O |
| Ia1.045 | $CH_3$ | $OC_2H_5$ | $CH_2$—C≡CH | O |
| Ia1.046 | $CH_3$ | H | $CH_3$ | NH |
| Ia1.047 | $CH_3$ | H | $C_2H_5$ | NH |
| Ia1.048 | $CH_3$ | H | $CH_2$—C≡CH | NH |
| Ia1.049 | $CH_3$ | $CH_3$ | $CH_3$ | NH |
| Ia1.050 | $CH_3$ | $CH_3$ | $C_2H_5$ | NH |
| Ia1.051 | $CH_3$ | $CH_3$ | $CH_2$—C≡CH | NH |
| Ia1.052 | $CH_3$ | $C_2H_5$ | $CH_3$ | NH |
| Ia1.053 | $CH_3$ | $C_2H_5$ | $C_2H_5$ | NH |
| Ia1.054 | $CH_3$ | $C_2H_5$ | $CH_2$—C≡CH | NH |
| Ia1.055 | $CH_3$ | $OCH_3$ | $CH_3$ | NH |
| Ia1.056 | $CH_3$ | $OCH_3$ | $C_2H_5$ | NH |
| Ia1.057 | $CH_3$ | $OCH_3$ | $CH_2$—C≡CH | NH |
| Ia1.058 | $CH_3$ | $OC_2H_5$ | $CH_3$ | NH |
| Ia1.059 | $CH_3$ | $OC_2H_5$ | $C_2H_5$ | NH |
| Ia1.060 | $CH_3$ | $OC_2H_5$ | $CH_2$—C≡CH | NH |
| Ia1.061 | $OCH_3$ | H | $CH_3$ | O |
| Ia1.062 | $OCH_3$ | H | $C_2H_5$ | O |
| Ia1.063 | $OCH_3$ | H | $CH_2$—C≡CH | O |

TABLE 1-continued

| No. | R² | R³ | R⁴ | X |
|---|---|---|---|---|
| Ia1.064 | OCH₃ | CH₃ | CH₃ | O |
| Ia1.065 | OCH₃ | CH₃ | C₂H₅ | O |
| Ia1.066 | OCH₃ | CH₃ | CH₂—C≡CH | O |
| Ia1.067 | OCH₃ | C₂H₅ | CH₃ | O |
| Ia1.068 | OCH₃ | C₂H₅ | C₂H₅ | O |
| Ia1.069 | OCH₃ | C₂H₅ | CH₂—C≡CH | O |
| Ia1.070 | OCH₃ | OCH₃ | CH₃ | O |
| Ia1.071 | OCH₃ | OCH₃ | C₂H₅ | O |
| Ia1.072 | OCH₃ | OCH₃ | CH₂—C≡CH | O |
| Ia1.073 | OCH₃ | OC₂H₅ | CH₃ | O |
| Ia1.074 | OCH₃ | OC₂H₅ | C₂H₅ | O |
| Ia1.075 | OCH₃ | OC₂H₅ | CH₂—C≡CH | O |
| Ia1.076 | OCH₃ | H | CH₃ | NH |
| Ia1.077 | OCH₃ | H | C₂H₅ | NH |
| Ia1.078 | OCH₃ | H | CH₂—C≡CH | NH |
| Ia1.079 | OCH₃ | CH₃ | CH₃ | NH |
| Ia1.080 | OCH₃ | CH₃ | C₂H₅ | NH |
| Ia1.081 | OCH₃ | CH₃ | CH₂—C≡CH | NH |
| Ia1.082 | OCH₃ | C₂H₅ | CH₃ | NH |
| Ia1.083 | OCH₃ | C₂H₅ | C₂H₅ | NH |
| Ia1.084 | OCH₃ | C₂H₅ | CH₂—C≡CH | NH |
| Ia1.085 | OCH₃ | OCH₃ | CH₃ | NH |
| Ia1.086 | OCH₃ | OCH₃ | C₂H₅ | NH |
| Ia1.087 | OCH₃ | OCH₃ | CH₂—C≡CH | NH |
| Ia1.088 | OCH₃ | OC₂H₅ | CH₃ | NH |
| Ia1.089 | OCH₃ | OC₂H₅ | C₂H₅ | NH |
| Ia1.090 | OCH₃ | OC₂H₅ | CH₂—C≡CH | NH |
| Ia1.091 | CF₃ | H | CH₃ | O |
| Ia1.092 | CF₃ | H | C₂H₅ | O |
| Ia1.093 | CF₃ | H | CH₂—C≡CH | O |
| Ia1.094 | CF₃ | CH₃ | CH₃ | O |
| Ia1.095 | CF₃ | CH₃ | C₂H₅ | O |
| Ia1.096 | CF₃ | CH₃ | CH₂—C≡CH | O |
| Ia1.097 | CF₃ | C₂H₅ | CH₃ | O |
| Ia1.098 | CF₃ | C₂H₅ | C₂H₅ | O |
| Ia1.099 | CF₃ | C₂H₅ | CH₂—C≡CH | O |
| Ia1.100 | CF₃ | OCH₃ | CH₃ | O |
| Ia1.101 | CF₃ | OCH₃ | C₂H₅ | O |
| Ia1.102 | CF₃ | OCH₃ | CH₂—C≡CH | O |
| Ia1.103 | CF₃ | OC₂H₅ | CH₃ | O |
| Ia1.104 | CF₃ | OC₂H₅ | C₂H₅ | O |
| Ia1.105 | CF₃ | OC₂H₅ | CH₂—C≡CH | O |
| Ia1.106 | CF₃ | H | CH₃ | NH |
| Ia1.107 | CF₃ | H | C₂H₅ | NH |
| Ia1.108 | CF₃ | H | CH₂—C≡CH | NH |
| Ia1.109 | CF₃ | CH₃ | CH₃ | NH |
| Ia1.110 | CF₃ | CH₃ | C₂H₅ | NH |
| Ia1.111 | CF₃ | CH₃ | CH₂—C≡CH | NH |
| Ia1.112 | CF₃ | C₂H₅ | CH₃ | NH |
| Ia1.113 | CF₃ | C₂H₅ | C₂H₅ | NH |
| Ia1.114 | CF₃ | C₂H₅ | CH₂—C≡CH | NH |
| Ia1.115 | CF₃ | OCH₃ | CH₃ | NH |
| Ia1.116 | CF₃ | OCH₃ | C₂H₅ | NH |
| Ia1.117 | CF₃ | OCH₃ | CH₂—C≡CH | NH |
| Ia1.118 | CF₃ | OC₂H₅ | CH₃ | NH |
| Ia1.119 | CF₃ | OC₂H₅ | C₂H₅ | NH |
| Ia1.120 | CF₃ | OC₂H₅ | CH₂—C≡CH | NH |
| Ia1.121 | SO₂CH₃ | H | CH₃ | O |
| Ia1.122 | SO₂CH₃ | H | C₂H₅ | O |
| Ia1.123 | SO₂CH₃ | H | CH₂—C≡CH | O |
| Ia1.124 | SO₂CH₃ | CH₃ | CH₃ | O |
| Ia1.125 | SO₂CH₃ | CH₃ | C₂H₅ | O |
| Ia1.126 | SO₂CH₃ | CH₃ | CH₂—C≡CH | O |
| Ia1.127 | SO₂CH₃ | C₂H₅ | CH₃ | O |
| Ia1.128 | SO₂CH₃ | C₂H₅ | C₂H₅ | O |
| Ia1.129 | SO₂CH₃ | C₂H₅ | CH₂—C≡CH | O |
| Ia1.130 | SO₂CH₃ | OCH₃ | CH₃ | O |
| Ia1.131 | SO₂CH₃ | OCH₃ | C₂H₅ | O |
| Ia1.132 | SO₂CH₃ | OCH₃ | CH₂—C≡CH | O |
| Ia1.133 | SO₂CH₃ | OC₂H₅ | CH₃ | O |
| Ia1.134 | SO₂CH₃ | OC₂H₅ | C₂H₅ | O |
| Ia1.135 | SO₂CH₃ | OC₂H₅ | CH₂—C≡CH | O |
| Ia1.136 | SO₂CH₃ | H | CH₃ | NH |
| Ia1.137 | SO₂CH₃ | H | C₂H₅ | NH |
| Ia1.138 | SO₂CH₃ | H | CH₂—C≡CH | NH |
| Ia1.139 | SO₂CH₃ | CH₃ | CH₃ | NH |
| Ia1.140 | SO₂CH₃ | CH₃ | C₂H₅ | NH |
| Ia1.141 | SO₂CH₃ | CH₃ | CH₂—C≡CH | NH |
| Ia1.142 | SO₂CH₃ | C₂H₅ | CH₃ | NH |
| Ia1.143 | SO₂CH₃ | C₂H₅ | C₂H₅ | NH |
| Ia1.144 | SO₂CH₃ | C₂H₅ | CH₂—C≡CH | NH |
| Ia1.145 | SO₂CH₃ | OCH₃ | CH₃ | NH |
| Ia1.146 | SO₂CH₃ | OCH₃ | C₂H₅ | NH |
| Ia1.147 | SO₂CH₃ | OCH₃ | CH₂—C≡CH | NH |
| Ia1.148 | SO₂CH₃ | OC₂H₅ | CH₃ | NH |
| Ia1.149 | SO₂CH₃ | OC₂H₅ | C₂H₅ | NH |
| Ia1.150 | SO₂CH₃ | OC₂H₅ | CH₂—C≡CH | NH |
| Ia1.151 | NO₂ | H | CH₃ | O |
| Ia1.152 | NO₂ | H | C₂H₅ | O |
| Ia1.153 | NO₂ | H | CH₂—C≡CH | O |
| Ia1.154 | NO₂ | CH₃ | CH₃ | O |
| Ia1.155 | NO₂ | CH₃ | C₂H₅ | O |
| Ia1.156 | NO₂ | CH₃ | CH₂—C≡CH | O |
| Ia1.157 | NO₂ | C₂H₅ | CH₃ | O |
| Ia1.158 | NO₂ | C₂H₅ | C₂H₅ | O |
| Ia1.159 | NO₂ | C₂H₅ | CH₂—C≡CH | O |
| Ia1.160 | NO₂ | OCH₃ | CH₃ | O |
| Ia1.161 | NO₂ | OCH₃ | C₂H₅ | O |
| Ia1.162 | NO₂ | OCH₃ | CH₂—C≡CH | O |
| Ia1.163 | NO₂ | OC₂H₅ | CH₃ | O |
| Ia1.164 | NO₂ | OC₂H₅ | C₂H₅ | O |
| Ia1.165 | NO₂ | OC₂H₅ | CH₂—C≡CH | O |
| Ia1.166 | NO₂ | H | CH₃ | NH |
| Ia1.167 | NO₂ | H | C₂H₅ | NH |
| Ia1.168 | NO₂ | H | CH₂—C≡CH | NH |
| Ia1.169 | NO₂ | CH₃ | CH₃ | NH |
| Ia1.170 | NO₂ | CH₃ | C₂H₅ | NH |
| Ia1.171 | NO₂ | CH₃ | CH₂—C≡CH | NH |
| Ia1.172 | NO₂ | C₂H₅ | CH₃ | NH |
| Ia1.173 | NO₂ | C₂H₅ | C₂H₅ | NH |
| Ia1.174 | NO₂ | C₂H₅ | CH₂—C≡CH | NH |
| Ia1.175 | NO₂ | OCH₃ | CH₃ | NH |
| Ia1.176 | NO₂ | OCH₃ | C₂H₅ | NH |
| Ia1.177 | NO₂ | OCH₃ | CH₂—C≡CH | NH |
| Ia1.178 | NO₂ | OC₂H₅ | CH₃ | NH |
| Ia1.179 | NO₂ | OC₂H₅ | C₂H₅ | NH |
| Ia1.180 | NO₂ | OC₂H₅ | CH₂—C≡CH | NH |

Furthermore, most particular preference is given to the following 2-benzoylcyclohexane-1,3-diones of the formula I:

the compounds Ia2, in particular the compounds Ia2.001–Ia2.180, which differ from the corresponding compounds Ia1.001-Ia1.180 in that $R^{13}$ is methyl:

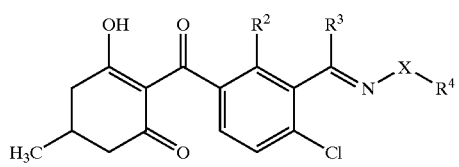
Ia2 the compounds Ia3, in particular the compounds Ia3.001–Ia3.180, which differ from the corresponding compounds Ia1.001–Ia1.180 in that $R^{13}$ and $R^{14}$ are each methyl:

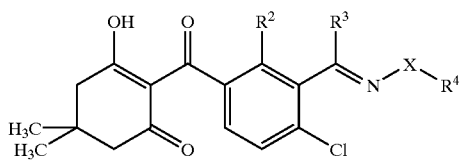
Ia3 the compounds Ia4, in particular the compounds Ia4.001–Ia4.180, which differ from the corresponding compounds Ia1.001–Ia1.180 in that $R^{15}$ and $R^{16}$ are each methyl:

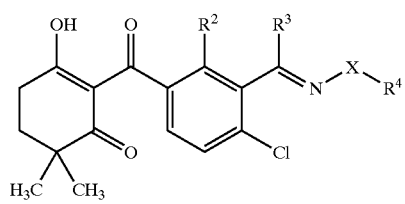
Ia4 the compounds Ia5, in particular the compounds Ia5.001–Ia5.180, which differ from the corresponding compounds Ia1.001–Ia1.180 in that the $CR^{13}R^{14}$ unit is replaced by C=O:

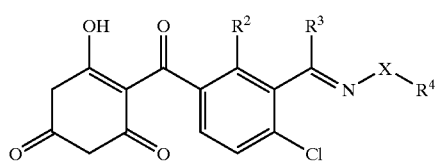
Ia5 the compounds Ia6, in particular the compounds Ia6.001–Ia6.180, which differ from the corresponding compounds Ia1.001–Ia1.180 in that $R^{11}$, $R^{15}$ and $R^{16}$ are each methyl and the $CR^{13}R^{14}$ unit is replaced by C=O:

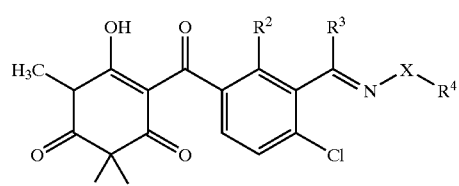
Ia6 the compounds Ia7, in particular the compounds Ia7.001–Ia7.180, which differ from the corresponding compounds Ia1.001–Ia1.180 in that $R^{11}$, $R^{12}$, $R^{15}$ and $R^{16}$ are each methyl and the $CR^{13}R^{14}$ unit is replaced by C=O:

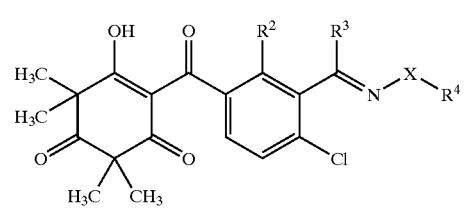
Ia7 the compounds Ia8, in particular the compounds Ia8.001–Ia8.180, which differ from the corresponding compounds Ia1.001–Ia1.180 in that $R^1$ is nitro:

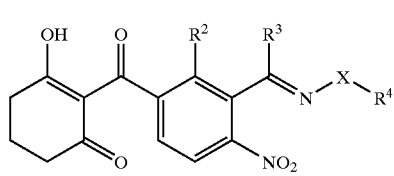
Ia8 the compounds Ia9, in particular the compounds Ia9.001–Ia9.180, which differ from the corresponding compounds Ia1.001–Ia1.180 in that $R^1$ is nitro and $R^{13}$ is methyl:

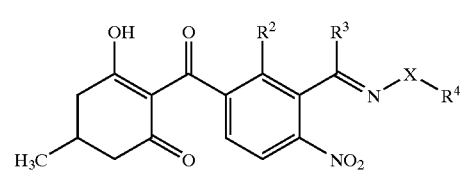
Ia9 the compounds Ia10, in particular the compounds Ia10.001–Ia10.180, which differ from the corresponding compounds Ia1.001–Ia1.180 in that $R^1$ is nitro and $R^{13}$ and $R^{14}$ are each methyl:

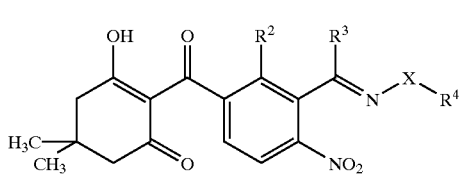
Ia10 the compounds Ia11, in particular the compounds Ia11.001–Ia11.180, which differ from the corresponding compounds Ia1.001–Ia1.180 in that $R^1$ is nitro and $R^{15}$ and $R^{16}$ are each methyl:

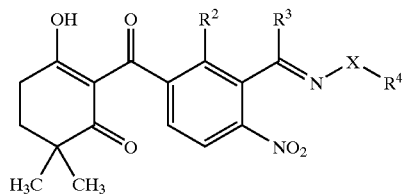
Ia11 the compounds Ia12, in particular the compounds Ia12.001–Ia12.180, which differ from the corresponding compounds Ia1.001–Ia1.180 in that $R^1$ is nitro and the $CR^{13}R^{14}$ unit is replaced by C=O:

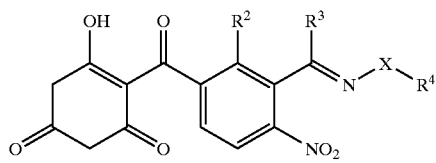
Ia12 the compounds Ia13, in particular the compounds Ia13.001–Ia13.180, which differ from the corresponding compounds Ia1.001–Ia1.180 in that $R^1$ is nitro, $R^{11}$, $R^{15}$ and $R^{16}$ are each methyl and the $CR^{13}R^{14}$ unit is replaced by C=O:

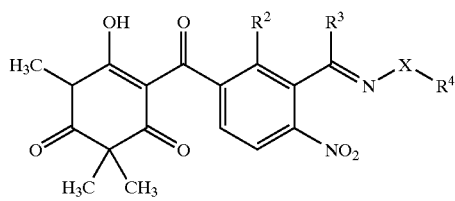
Ia13 the compounds Ia14, in particular the compounds Ia14.001–Ia14.180, which differ from the corresponding compounds Ia1.001–Ia1.180 in that $R^1$ is nitro, $R^{11}$, $R^{12}$, $R^{15}$ and $R^{16}$ are each methyl and the $CR^{13}R^{14}$ unit is replaced by C=O:

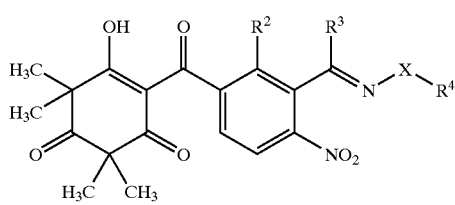
Ia14 the compounds Ia15, in particular the compounds Ia15.001–Ia15.180, which differ from the corresponding compounds Ia1.001–Ia1.180 in that $R^1$ is methylsulfonyl:

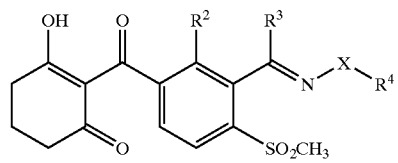
Ia15 the compounds Ia16, in particular the compounds Ia16.001–Ia16.180, which differ from the corresponding compounds Ia1.001–Ia1.180 in that $R^1$ is methylsulfonyl and $R^{13}$ is methyl:

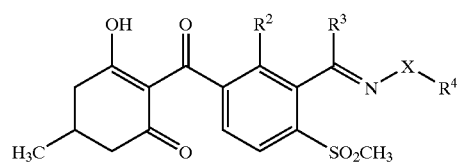
Ia16 the compounds Ia17, in particular the compounds Ia17.001–Ia17.180, which differ from the corresponding compounds Ia1.001–Ia1.180 in that $R^1$ is methylsulfonyl and $R^{13}$ and $R^{14}$ are each methyl:

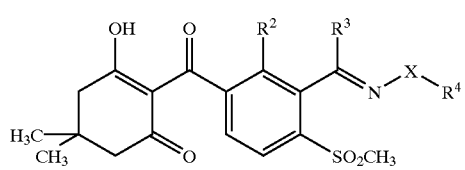
Ia17 the compounds Ia18, in particular the compounds Ia18.001–Ia18.180, which differ from the corresponding compounds Ia1.001–Ia1.180 in that $R^1$ is methylsulfonyl and $R^{15}$ and $R^{16}$ are each methyl:

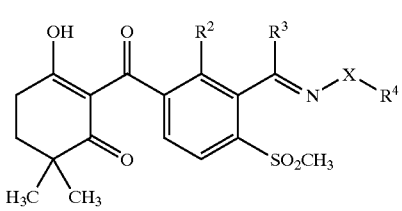
Ia18 the compounds Ia19, in particular the compounds Ia19.001–Ia19.180, which differ from the corresponding compounds Ia1.001–Ia1.180 in that $R^1$ is methylsulfonyl and the $CR^{13}R^{14}$ unit is replaced by C=O:

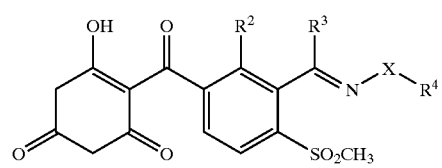
Ia19 the compounds Ia20, in particular the compounds Ia20.001–Ia20.180, which differ from the corresponding compounds Ia1.001–Ia1.180 in that $R^1$ is methylsulfonyl, $R^{11}$, $R^{15}$ and $R^{16}$ are each methyl and the $CR^{13}R^{14}$ unit is replaced by C=O:

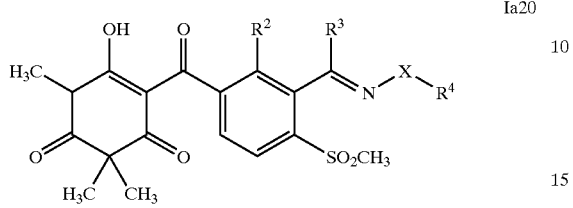

Ia20 the compounds Ia21, in particular the compounds Ia21.001–Ia21.180, which differ from the corresponding compounds Ia1.001–Ia1.180 in that $R^1$ is methylsulfonyl, $R^{11}$ $R^{12}$ $R^{15}$ and $R^{16}$ are each methyl and the $CR^{13}R^{14}$ unit is replaced by C=O:

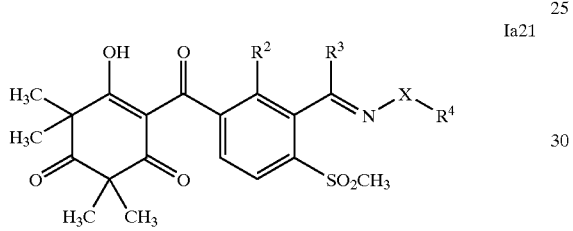

Ia21 the compounds Ia22, in particular the compounds Ia22.001–Ia22.180, which differ from the corresponding compounds Ia1.001–Ia1.180 in that $R^1$ is trifluoromethyl:

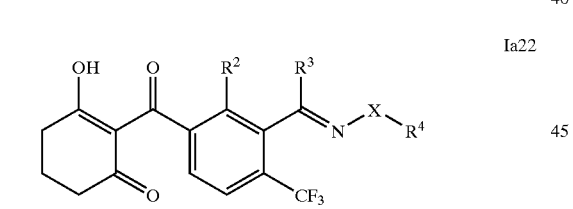

Ia22 the compounds Ia23, in particular the compounds Ia23.001–Ia23.180, which differ from the corresponding compounds Ia1.001–Ia1.180 in that $R^1$ is trifluoromethyl and $R^{13}$ is methyl:

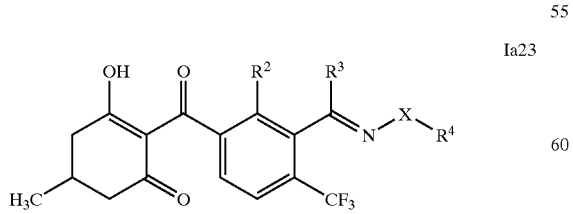

Ia23 the compounds Ia24, in particular the compounds Ia24.001–Ia24.180, which differ from the corresponding compounds Ia1.001–Ia1.180 in that $R^1$ is trifluoromethyl and $R^{13}$ and $R^{14}$ are each methyl:

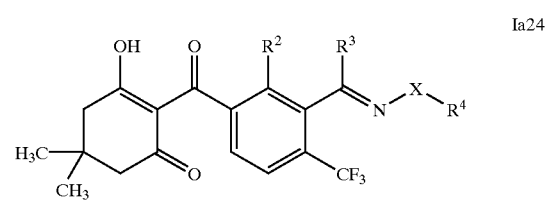

Ia24 the compounds Ia25, in particular the compounds Ia25.001–Ia25.180, which differ from the corresponding compounds Ia1.001–Ia1.180 in that $R^1$ is trifluoromethyl and $R^{15}$ and $R^{16}$ are each methyl:

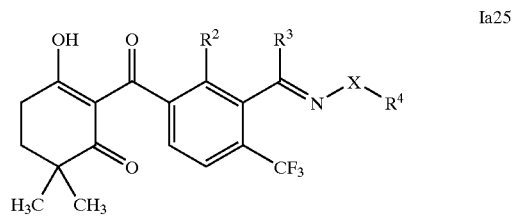

Ia25 the compounds Ia26, in particular the compounds Ia26.001–Ia26.180, which differ from the corresponding compounds Ia1.001–Ia1.180 in that $R^1$ is trifluoromethyl and the $CR^{13}R^{14}$ unit is replaced by C=O:

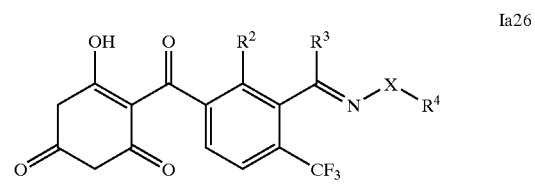

Ia26 the compounds Ia27, in particular the compounds Ia27.001–Ia27.180, which differ from the corresponding compounds Ia1.001–Ia1.180 in that $R^1$ is trifluoromethyl, $R^{11}$, $R^{15}$ and $R^{16}$ are each methyl and the $CR^{13}R^{14}$ unit is replaced by C=O:

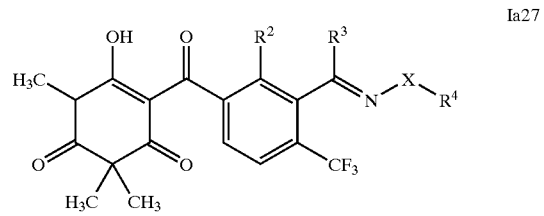

Ia27 the compounds Ia28, in particular the compounds Ia28.001–Ia28.180, which differ from the corresponding compounds Ia1.001–Ia1.180 in that $R^1$ is trifluoromethyl, $R^{11}$, $R^{12}$, $R^{15}$ and $R^{16}$ are each methyl and the $CR^{13}R^{14}$ unit is replaced by C=O:

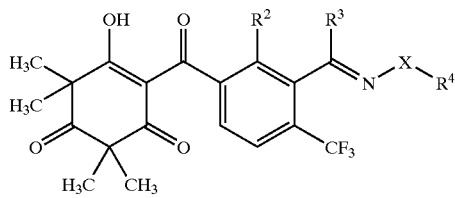

Extraordinary preference is given to the compounds of the formula Ia' ≙ I where $R^1$ is attached in position 4 of the phenyl ring and $R^2$ is attached in position 2 of the phenyl ring)

where
- $R^1$ is halogen or $C_1$–$C_4$-alkylsulfonyl;
- $R^2$ is halogen or $C_1$–$C_4$-alkyl, in particular halogen;
- $R^3$ is hydrogen, $C_1$–$C_4$-alkyl or $C_1$–$C_4$-alkoxy, in particular hydrogen or $C_1$–$C_4$-alkoxy;
- $R^4$ is $C_1$–$C_6$-alkyl, $C_3$–$C_6$-alkynyl, where these two substituents may be partially or fully halogenated and/or may carry one to three of the following groups: phenyl or hetaryl, where these groups may in turn be partially or fully halogenated;
- X is oxygen;
- $R^{11}$, $R^{12}$, $R^{13}$, $R^{14}$, $R^{15}$, $R^{16}$ are each hydrogen or $C_1$–$C_4$-alkyl.

The 2-benzoylcyclohexane-1,3-diones of the formula I can be obtained in a variety of ways, for example by the following process:

Reaction of cyclohexanediones of the formula II with an activated carboxylic acid IIIα or a carboxylic acid IIIβ which is preferably activated in situ, to give the acylation product IV, and activated subsequent rearrangement.

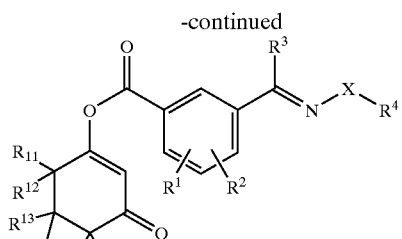

L is a nucleophilically replaceable leaving group, such as halogen, for example bromine or chlorine, hetaryl, for example imidazolyl or pyridyl, carboxylate, for example acetate or trifluoroacetate, etc.

The activated carboxylic acid can be employed directly, as in the case of the acyl halides, or be generated in situ, for example by using dicyclohexylcarbodiimide, triphenylphosphine/azodicarboxylic acid esters, 2 pyridine disulfite [sic]/triphenylphosphine, carbonyldiimidazole, etc.

If appropriate, it may be advantageous to carry out the acylation reaction in the presence of a base. The reactants and the auxiliary base are advantageously employed in equimolar amounts. A slight excess of the auxiliary base, for example 1.2 to 1.5 molar equivalents based on II, may be advantageous in certain instances.

Suitable auxiliary bases are tertiary alkylamines, pyridine or alkali metal carbonates. Suitable solvents are, for example, chlorinated hydrocarbons, such as methylene chloride and 1,2-dichloroethane, aromatic hydrocarbons, such as toluene, xylene or chlorobenzene, ethers, such as diethyl ether, methyl tert-butyl ether, tetrahydrofuran and dioxane, polar aprotic solvents, such as acetonitrile, dimethylformamide and dimethyl sulfoxide, or esters such as ethyl acetate, or mixtures of these.

If acyl halides are used as activated carboxylic acid component, it may be advantageous to cool the reaction mixture to 0–10° C. when adding this reaction partner. Subsequently, the mixture is stirred at 20–100° C., preferably at 25–50° C., until the reaction has ended. Work-up is carried out in a conventional manner, for example by pouring the reaction mixture into water and extracting the product of value. Suitable solvents for this purpose are in particular methylene chloride, diethyl ether and ethyl acetate. After drying off the organic phase and removal of the solvent, crude enol ester of the formula IV is preferably purified by chromatography. However, it is also possible to use the crude enol ester of the formula IV without further purification for the rearrangement.

The rearrangement of the enol esters of the formula IV to the compounds of the formula I is advantageously carried out at temperatures from 20 to 40° C. in a solvent and in the presence of an auxiliary base and, if appropriate, with the aid of a cyano compound as catalyst.

Suitable solvents are, for example, acetonitrile, methylene chloride, 1,2-dichloroethane, ethyl acetate, toluene or mixtures of these. The preferred solvent is acetonitrile.

Suitable auxiliary bases are tertiary amines such as triethylamine or pyridine, or alkali metal carbonates, such as sodium carbonate and potassium carbonate, which are preferably employed in equimolar amounts or in up to four-fold excess, based on the enol ester. Preference is given to using triethylamine, preferably in twice the equimolar amount, based on the enol ester.

Suitable "rearrangement catalysts" are inorganic cyanides, such as sodium cyanide and potassium cyanide, and organic cyano compounds, such as acetone cyanohydrin and trimethylsilyl cyanide. They are conventionally used in an amount of from 1 to 50 mol percent, based on the enol ester. Preference is given to using acetone cyanohydrin or trimethylsilyl cyanide, for example in an amount of from 5 to 15, preferably 10, mol percent, based on the enol ester.

Workup can be carried out in a manner known per se. For example, the reaction mixture is acidified with dilute mineral acid, such as, for example 5% strength hydrochloric acid or sulfuric acid, and extracted with an organic solvent, for example methylene chloride or ethyl acetate. The organic extract may be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, dried and concentrated.

(Examples of the preparation of enol esters from cyclohexane-1,3-diones and of the cyanide-catalyzed rearrangement of the enol esters are given, for example, in EP-A 186 118, U.S. Pat. No. 4,780,127).

The cyclohexane-1,3-diones of the formula II used as starting materials are known or can be prepared by known processes (for example EP-A 71 707, EP-A 142 741, EP-A 243 313, U.S. Pat. No. 4,249,937; WO 92/13821).

The benzoic acid derivatives of the formula III are novel,

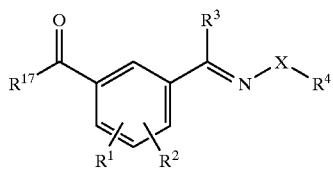

III where:
- $R^1$, $R^2$ are each hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$, —$OCOR^6$, —$OSO_2R^6$, —SH, —$S(O)_nR^7$, —$SO_2OR^5$, —$SO_2NR^5R^8$, —$NR^8SO_2R^6$ or —$NR^8COR^6$;
- $R^3$ is hydrogen, cyano, $C_1$–$C_6$-alkyl, $C_1$–$C_6$-haloalkyl, —$OR^7$, —$SR^7$ or —$NR^7R^{10}$;
- $R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, where the alkyl, cycloalkyl, alkenyl, cycloalkenyl and alkynyl radicals mentioned and $R^9$ of the radicals —$COR^9$, —$CO_2R^9$, —$COSR^9$ and —$CONR^8R^9$ may be partially or fully halogenated and/or carry one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

- X is oxygen or $NR^8$;
- n is 0, 1 or 2;
- $R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
- $R^6$ is $C_1$–$C_6$-alkyl or $C_1$–$C_6$-haloalkyl;
- $R^7$ is $C_1$–$C_6$-alkyl, $C_1$–$C_6$-haloalkyl, $C_4$–$C_6$-alkoxy-$C_2$–$C_6$-alkyl, $C_3$–$C_6$-alkenyl or $C_3$–$C_6$-alkynyl;
- $R^8$ is hydrogen or $C_1$–$C_6$-alkyl;
- $R^9$ is $C_1$–$C_6$-alkyl, $C_3$–$C_6$-alkenyl, $C_3$–$C_6$-alkynyl, phenyl or benzyl;
- $R^{10}$ is $C_1$–$C_6$-alkyl, $C_1$–$C_6$-haloalkyl, $C_3$–$C_6$-alkenyl or $C_3$–$C_6$-alkynyl;
- $R^{17}$ is hydroxyl or a radical that can be removed by hydrolysis.

Examples of radicals that can be removed by hydrolysis are alkoxy, phenoxy, alkylthio and phenylthio radicals with or without substitution, halides, hetaryl radicals which are attached via nitrogen, amino and imino radicals with or without substitution, etc.

Preference is given to benzoyl halides IIIα, where L=halogen ≙ III where $R^{17}$=halogen),

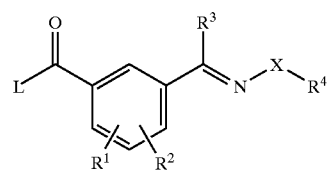

IIIα where the variables $R^1$ to $R^4$ and X are each as defined under formula III and L is halogen, in particular chloride or bromide.

Preference is also given to the benzoic acids of the formula IIIβ ≙ III where $R^{17}$=hydroxyl),

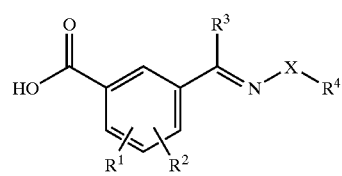

IIIβ where the variables $R^1$ to $R^4$ and X are each as defined under formula III.

Preference is also given to the benzoic acid esters of the formula IIIγ (≙ III where M=$C_1$–$C_6$-alkoxy)

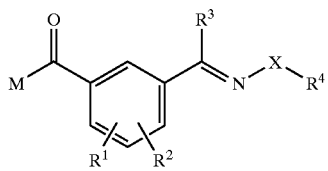

IIIγ where the variables $R^1$ to $R^4$ and X are each as defined under formula III and M is $C_1$–$C_6$-alkoxy.

With regard to the preferred compounds of the formula III, the remarks made under the compounds I apply to the radicals $R^1$ to $R^4$ and X.

The compounds of the formula IIIα (where L=halogen) can be prepared in a similar manner to literature methods (cf. L. G. Fieser, M. Fieser "Reagents for Organic Synthesis", Vol. I, p. 767–769 (1967)) by reacting benzoic acids of the formula IIIβ with halogenating reagents such as thionyl chloride, thionyl bromide, phosgene, diphosgene, triphosgene, oxalyl chloride or oxalyl bromide.

The benzoic acids of the formula IIIβ can be obtained in a similar manner to literature methods, inter alia by hydrolysis of the benzoic acid esters of the formula IIIγ (where M=$C_1$–$C_6$-alkoxy).

The benzoic acid esters of the formula IIIγ are obtainable in a variety of ways, for example by the following processes:

A)

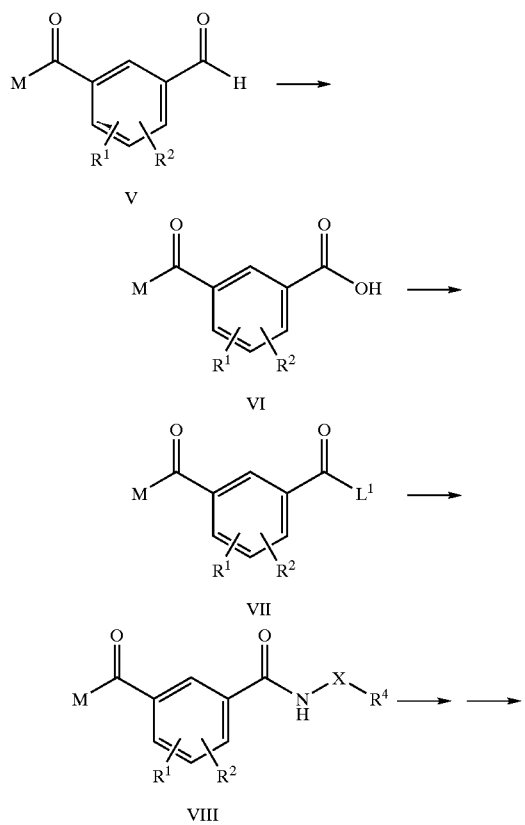

V

VI

VII

VIII

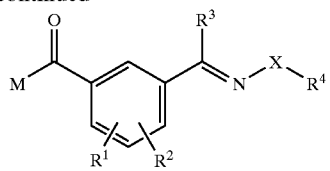

IIIγ (where $R^3$ = $OR^7$)

Isophthalic acid derivatives of the formula VI can be obtained by oxidation of aldehydes of the formula V in a manner known per se (J. March, "Advanced Organic Chemistry", 3rd Edition, p. 629 ff, Wiley-Interscience Publication, 1985).

In a similar manner to literature methods, the compounds of the formula VI can initially be converted into the corresponding activated carboxylic acids VII where $L^1$ is a nucleophilically displaceable leaving group such as halogen, for example bromine or chlorine, hetaryl, for example imidazolyl or pyridyl, carboxylate, for example acetate or trifluoracetate etc., and then into the corresponding hydroxamic acid or carbohydrazide derivatives of the formula VIII (Australian J. Chem. 22, (1969), 1731–1735; ibid 22 (1969), 161–173; J. Org. Chem. 27 (1974), 1341–1349).

Alkylation of compounds of the formula VIII leads to compounds of the formula IIIγ (where $R^3$=$OR^7$) in a manner known per se (EP-A 463 989; Synthesis (1983), 220–222; U.S. Pat. No. 4,931,088; J. Org. Chem. 31 (1971), 284–294; J. Chem. Soc. Perk. II (1977), 1080–1084).

B)

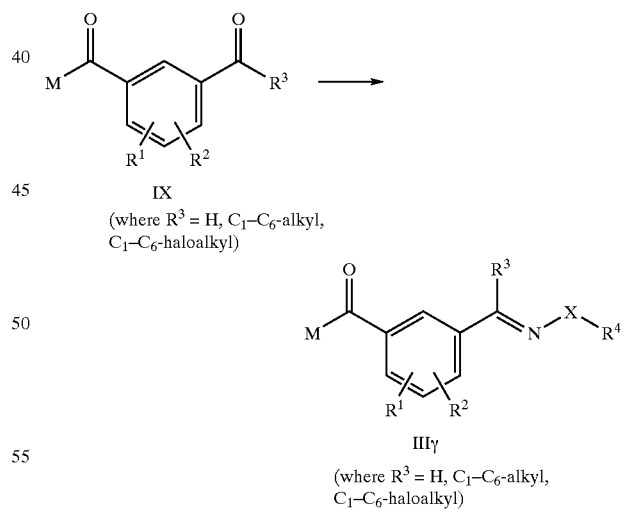

IX
(where $R^3$ = H, $C_1$–$C_6$-alkyl, $C_1$–$C_6$-haloalkyl)

IIIγ
(where $R^3$ = H, $C_1$–$C_6$-alkyl, $C_1$–$C_6$-haloalkyl)

Compounds of the formula IIIγ are obtained in a manner known per se by reacting aldehydes/ketones of the formula IX with "alkoxamines or alkylhydrazines". In a similar manner to processes known from the literature, it is possible to react aldehydes/ketones of the formula IX with hydroxylamine or hydrazine and to alkylate them subsequently (J. March, "Advanced Organic Chemistry", 3rd Edition, p. 359, p. 805–806, Wiley-Interscience Publication, 1985).

C)

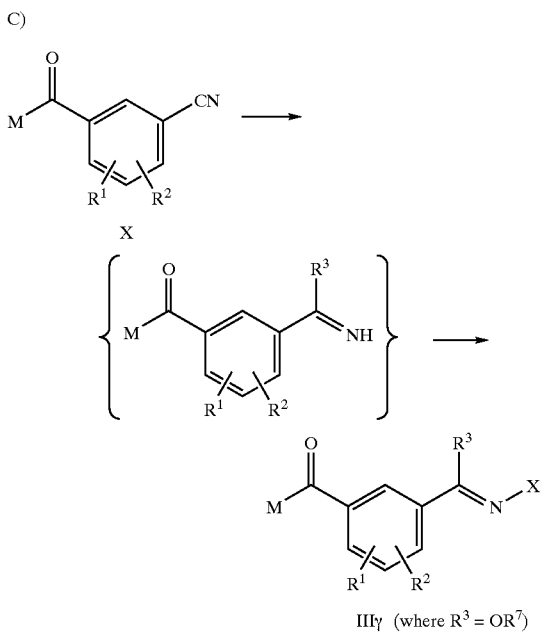

IIIγ (where $R^3 = OR^7$)

It is possible to convert nitriles of the formula X in a manner known per se by alcoholysis ($R^7OH$) into imino esters which can be reacted in a further step with hydroxylamines or hydrazines to give compounds of the formula IIIγ (J. March, "Advanced Organic Chemistry", 3rd Edition, p. 792–793, Wiley-Interscience Publication, 1985; U.S. Pat. No. 4,965,390).

In a similar manner to processes known from the literature, nitriles of the formula X can be prepared from the corresponding aldehydes V (J. March, "Advanced Organic Chemistry", 3rd Edition, p. 806–807, Wiley-Interscience Publication, 1985). It is also possible to obtain nitrites of the formula X from anilines of the formula XI by employing the Sandmeyer reaction or from aryl halides of the formula XII by the Rosemund/von Braun reaction using metal cyanides, in particular CuCN (J. March, "Advanced Organic Chemistry", 3rd Edition, p. 594, p. 648, Wiley-Interscience Publication, 1985).

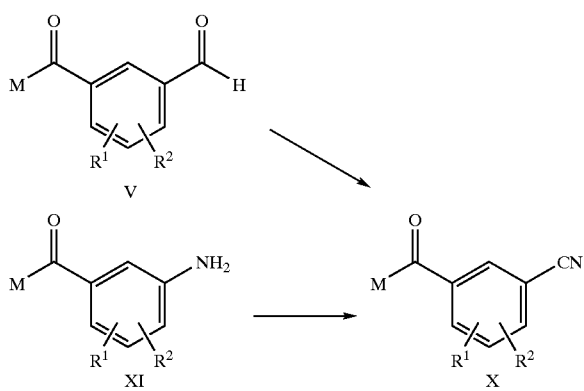

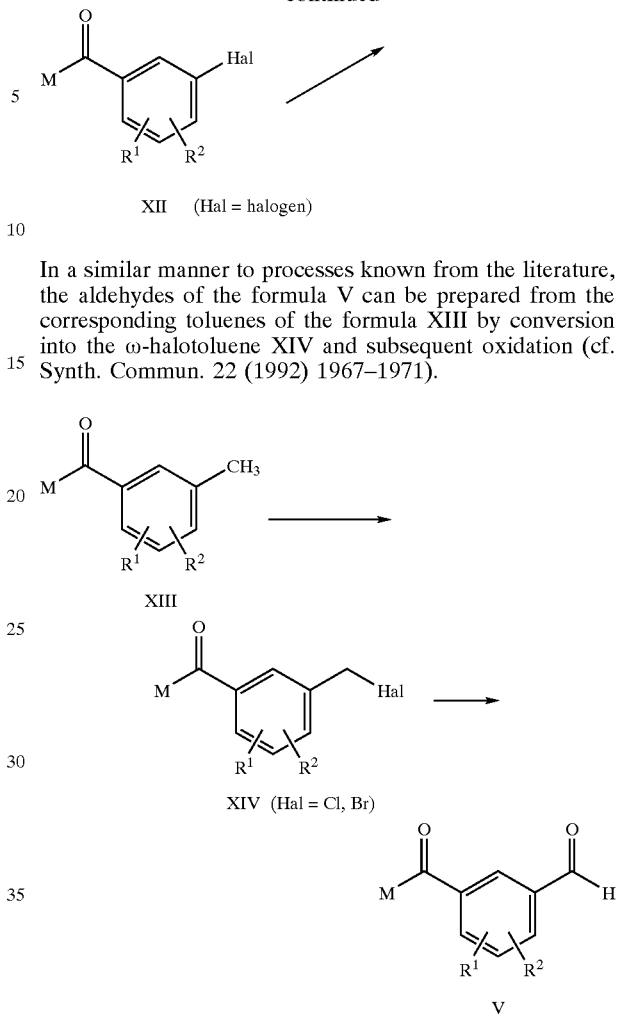

XII (Hal = halogen)

In a similar manner to processes known from the literature, the aldehydes of the formula V can be prepared from the corresponding toluenes of the formula XIII by conversion into the ω-halotoluene XIV and subsequent oxidation (cf. Synth. Commun. 22 (1992) 1967–1971).

XIV (Hal = Cl, Br)

PREPARATION EXAMPLES 2-(2,4-Dichloro-3-propargyloxyiminomethylbenzoyl)-5,5-dimethyl-1,3-cyclohexanedione (compound 2.12)

1.20 g (0.0086 mol) of dimedone and 1.80 g (0.0086 mol) of dicyclohexylcarbodiimide were added to a solution of 2.50 g (0.0092 mol) of 2,4-dichloro-3-propargyloxyiminomethyl-benzoic acid in 120 ml of dry acetonitrile. After stirring for 12 hours at room temperature, the mixture was filtered through silica gel (eluent:toluene), the solvent was then removed and the residue was taken up in 100 ml of dry acetonitrile and admixed with 0.40 g (0.0047 mol) of acetone cyanohydrin and 3.10 g (0.031 mol) of triethylamine. The reaction mixture was then stirred for 3 hours at room temperature and subsequently added to a mixture of 200 ml of water and 100 ml of 5% strength potassium carbonate solution. The aqueous phase was washed three times with ethyl acetate, then adjusted to pH=2 using 10% strength hydrochloric acid and extracted three times with ethyl acetate. The combined organic phases were washed with water until neutral, dried and concentrated. 0.7 g of 2-(2,4-dichloro-3-propargyloxyimino-methylbenzoyl)-5,5-dimethyl-cyclohexanedione was obtained.

($^1$H-NMR (CDCl$_3$, δ in ppm): 1.13 (6H); 2.32 (2H); 2.52 (1H); 2.66 (2H); 4.81 (2H); 7.12 (1H); 7.43 (1H); 8.31 (1H);

16.48 (1H).) 2-(2-Chloro-3-ethoxyiminomethyl-4-methylsulfonylbenzoyl)-5,5-dimethyl-1,3-cyclohexanedione (compound 2.07)

1.26 g (0.009 mol) of dimedone and 1.90 g (0.009 mol) of dicyclohexylcarbodiimide were added to a solution of 2.95 g (0.009 mol) of 2-chloro-3-ethoxyiminomethyl-4-methylsulfonyl-benzoic acid in 130 ml of anhydrous acetonitrile. After stirring for 12 hours at room temperature, 0.42 g (0.005 mol) of acetone cyanohydrin and 3.27 g (0.032 mol) of triethylamine in 10 ml of absolute acetonitrile were added dropwise. The reaction mixture was then stirred for a further 2 hours at room temperature. With stirring, the reaction mixture was poured into 200 ml of water, the precipitate was filtered off with suction and the filtrate was added to 100 ml of 5% strength potassium carbonate solution. The aqueous phase was washed with ethyl acetate, the pH was adjusted to 2 using 10% strength hydrochloric acid and the mixture was extracted with ethyl acetate. The combined organic phases were washed with water until neutral, dried and concentrated under reduced pressure. This gave 2.52 g of crude product which was recrystallized from toluene. (mp.: 156–157° C.)

2-[2,4-Dichloro-3-(1'-methoxyimino-1'-(methoxy)methyl)benzoyl]-1,3-cyclohexanedione (compound 2.10)

1.125 g (0.0038 mol) of 2,4-dichloro-3(1'-methoxyimino-1'-(methoxy)methyl)benzoyl chloride were added to a solution of 0.46 g (0.0045 mol) of triethylamine and 0.5 g (0.0045 mol) of 1,3-cyclohexanedione in 50 ml of methylene chloride. The reaction solution was stirred at room temperature for 2 hours and the solvent was then removed under reduced pressure. The residue was purified by silica gel chromatography (eluent:toluene/ethyl acetate=1/1). The enol ester obtained in this manner was taken up in 50 ml of acetonitrile and admixed with 0.80 g (0.008 mol) of triethylamine and 0.15 g (0.0015 mol) of trimethylsilyl cyanide. After stirring for 12 hours at room temperature, the solvent was removed and the residue was taken up in methylene chloride. The organic phase was washed with dilute phosphoric acid, dried and concentrated. This gave 0.90 g of 2-[2,4-dichloro-3-(1'-methoxyimino-1'-(methoxy)methyl)benzoyl]-1,3-cyclohexanedione which was digested with diethyl ether. (mp.: 180–182° C.)

In addition to the above-described benzoyl derivatives of the formula I, further compounds prepared or preparable in a similar manner are listed in Table 2 below:

TABLE 2

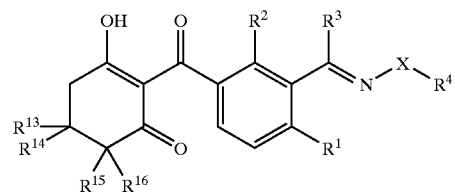

Ia (where $R^{11}$, $R^{12}$ = H)

| No. | X | $R^1$ | $R^2$ | $R^3$ | $R^4$ | $R^{13}$ | $R^{14}$ | $R^{15}$ | $R^{16}$ | Physical data mp. [° C.]; $^1$H NMR [ppm] |
|---|---|---|---|---|---|---|---|---|---|---|
| 2.01 | O | Cl | Cl | H | CH$_3$ | H | H | H | H | 177–185 |
| 2.02 | O | Cl | Cl | H | CH$_3$ | CH$_3$ | H | H | H | 106–108 |
| 2.03 | O | Cl | Cl | H | CH$_3$ | CH$_3$ | CH$_3$ | H | H | 158–160 |
| 2.04 | O | Cl | Cl | H | CH$_3$ | H | H | CH$_3$ | CH$_3$ | 1.15(6H); 1.84(2H); 2.78(2H); 3.97(3H); 7.08(1H); 7.39(1H); 8.22(1H); 16.81(1H) |
| 2.05 | O | Cl | Cl | OC$_2$H$_5$ | n-C$_3$H$_7$ | H | H | H | H | 140–142 |
| 2.06 | O | Cl | Cl | H | C$_2$H$_5$ | CH$_3$ | H | H | H | 114–115 |
| 2.07 | O | SO$_2$CH$_3$ | Cl | H | C$_2$H$_5$ | CH$_3$ | CH$_3$ | H | H | 156–157 |
| 2.08 | O | Cl | Cl | H | C$_2$H$_5$ | CH$_3$ | CH$_3$ | H | H | 1.15(6H); 1.33(3H); 2.32(2H); 2.64(2H); 4.23(2H); 7.12(1H); 7.43(1H); 8.23(1H); 16.95(1H) |
| 2.09 | O | Cl | Cl | OCH$_3$ | CH$_2$-4-Cl—C$_6$H$_4$ | CH$_3$ | CH$_3$ | H | H | 138–142 |
| 2.10 | O | Cl | Cl | OCH$_3$ | CH$_3$ | H | H | H | H | 180–182 |
| 2.11 | O | Cl | Cl | H | CH$_2$C≡CH | H | H | H | H | 2.20(2H); 2.55(1H); 2.64(2H); 3.03(2H); 4.85(2H); 7.44(1H); 8.19(1H); 8.52(1H); 16.92(1H) |
| 2.12 | O | Cl | Cl | H | CH$_2$C≡CH | CH$_3$ | CH$_3$ | H | H | 1.13(6H); 2.32(2H); 2.52(1H); 2.66(2H); 4.81(2H); 7.12(1H); 7.43(1H); 8.31(1H); 16.48(1H) |
| 2.13 | O | Cl | Cl | OCH$_3$ | n-C$_3$H$_7$ | H | H | H | H | 78–80 |
| 2.14 | O | Cl | Cl | OCH$_3$ | CH$_2$-4-Cl—C$_6$H$_4$ | H | H | H | H | 157–158 |
| 2.15 | O | SO$_2$CH$_3$ | Cl | H | CH$_3$ | H | H | H | H | 55–60 |
| 2.16 | O | SO$_2$CH$_3$ | Cl | H | C$_2$H$_5$ | CH$_3$ | CH$_3$ | H | H | 95–100 |
| 2.17 | O | SO$_2$CH$_3$ | Cl | CH$_3$ | CH$_3$ | CH$_3$ | H | H | H | |
| 2.18 | O | SO$_2$CH$_3$ | Cl | CH$_3$ | CH$_3$ | CH$_3$ | CH$_3$ | H | H | |
| 2.19 | O | SO$_2$CH$_3$ | Cl | CH$_3$ | CH$_3$ | H | H | H | H | |
| 2.20 | O | SO$_2$CH$_3$ | CH$_3$ | CH$_3$ | CH$_3$ | H | H | H | H | 145–151 |
| 2.21 | O | SO$_2$CH$_3$ | CH$_3$ | CH$_3$ | CH$_3$ | CH$_3$ | H | H | H | |
| 2.22 | O | SO$_2$CH$_3$ | CH$_3$ | CH$_3$ | CH$_3$ | CH$_3$ | CH$_3$ | H | H | 190–192 |

The syntheses of some starting materials are listed below:

2-Chloro-3-ethoxyiminomethyl-4-methylsulfonylbenzoic acid (compound 3.04)

Step a) 2-Chloro-3-methyl-4-methylthioacetophenone

At 15–20° C., a solution of 157 g (2 mol) of acetyl chloride in 420 ml of 1,2-dichloroethane was added dropwise to a suspension of 286 g (2.14 mol) of aluminum trichloride in 420 ml of 1,2-dichloroethane. A solution of 346 g (2 mol) of 2-chloro-6-methylthiotoluene in 1 l of 1,2-dichloroethane was then added dropwise. After stirring for 12 hours, the reaction mixture was poured into a mixture of 3 l of ice and 1 l of concentrated HCl. The mixture was extracted with methylene chloride and the organic phase was washed with water, dried with sodium sulfate and concentrated. The residue was distilled under reduced pressure. 256 g (60% of theory) of 2-chloro-3-methyl-4-methylthioacetophenone were obtained.

(mp.: 46° C.)

Step b) 2-Chloro-3-methyl-4-methylsulfonylacetophenone 163.0 g (0.76 mol) of 2-chloro-3-methyl-4-methylthioacetophenone were dissolved in 1.5 l of glacial acetic acid and mixed with 18.6 g of sodium tungstate. With cooling, 173.3 g of a 30% strength hydrogen peroxide solution were added dropwise. Stirring was continued for a further 2 days and the mixture was then diluted with water. The precipitated solid was filtered off with suction, washed with water and dried. 164.0 g (88% of theory) of 2-chloro-3-methyl-4-methylsulfonylacetophenone were obtained.

(mp.: 110–111° C.)

Step c) 2-Chloro-3-methyl-4-methylsulfonylbenzoic acid 82 g (0.33 mol) of 2-chloro-3-methyl-4-methylsulfonylacetophenone were dissolved in 700 ml of dioxane and treated with 1 l of a 12.5% strength sodium hypochlorite solution at room temperature. The mixture was then stirred for 1 hour at 80° C. After cooling, two phases formed, the lower one of which was diluted with water and acidified slightly. The precipitated solid was filtered off with suction, washed with water and dried. 60 g (73% of theory) of 2-chloro-3-methyl-4-methylsulfonylbenzoic acid were obtained.

(mp.: 230–231° C.)

Step d) Methyl 2-chloro-3-methyl-4-methylsulfonylbenzoate 100 g (0.4 mol) of 2-chloro-3-methyl-4-methyl-sulfonylbenzoic acid were dissolved in 1 l of methanol and treated with hydrogen chloride gas for 5 hours at reflux temperature. The mixture was then concentrated. This gave 88.5 g (84% of theory) of methyl 2-chloro-3-methyl-4-methylsulfonylbenzoate.

(mp.: 107–108° C.)

Step e) Methyl 3-bromomethyl-2-chloro-4-methylsulfonylbenzoate 82 g (0.31 mol) of methyl 2-chloro-3-methyl-4-methylsulfonylbenzoate were dissolved in 2 l of carbon tetrachloride and, with exposure to light, admixed a little at a time with 56 g (0.31 mol) of N-bromosuccinimide. The reaction mixture was filtered, the filtrate was concentrated and the residue was taken up in 200 ml of methyl tert-butyl ether. The solution was admixed with petroleum ether and the precipitated solid was filtered off with suction and dried. 74.5 g (70% of theory) of methyl 3-bromomethyl-2-chloro-4-methylsulfonylbenzoate were obtained.

(mp.: 74–75° C.)

Step f) Methyl 2-chloro-3-formyl-4-methylsulfonylbenzoate

A solution of 41.0 g (0.12 mol) of methyl 3-bromomethyl-2-chloro-4-methylsulfonylbenzoate in 250 ml of acetonitrile was admixed with 42.1 g (0.36 mol) of N-methylmorpholine N-oxide. The reaction mixture was stirred for 12 hours at room temperature and then concentrated, and the residue was taken up in ethyl acetate. The solution was extracted with water, dried with sodium sulfate and concentrated. 31.2 g (94% of theory) of methyl 2-chloro-3-formyl-4-methylsulfonylbenzoate were obtained.

(mp.: 98–105° C.)

Step g) 2-Chloro-3-formyl-4-methylsulfonylbenzoic acid

At reflux temperature, a solution of 5.00 g (0.018 mol) of methyl 2-chloro-3-formyl-4-methylsulfonylbenzoate was added dropwise to a solution of 9.60 g (0.072 mol) of lithium iodide and 70 ml of dry pyridine. After stirring under reflux for 2 hours, the reaction mixture was cooled and the solvent was removed under reduced pressure. The residue was then taken up in water and adjusted to pH 1–2 with dilute hydrochloric acid. The aqueous phase was extracted with ethyl acetate and the combined organic phases were washed with water until neutral, dried and concentrated. 4.00 g of 2-chloro-3-formyl-4-methylsulfonylbenzoic acid (85% yield) were obtained.

($^1$H NMR (d$^6$-DMSO, δ in ppm): 3.41 (s, 3H); 8.05 (d, 1H); 8.11 (d, 1H); 10.49 (s, 1H); 14.21 (s, br., 1H).)

Step h) 2-Chloro-3-ethoxyiminomethyl-4-methylsulfonylbenzoic acid 1.63 g (0.017 mol) of O-ethylhydroxylamine hydrochloride and 1.15 g (0.0085 mol) of finely powdered potassium carbonate were stirred for 1 hour in 60 ml of dry methanol. 4.00 g (0.015 mol) of 2-chloro-3-formyl-4-methylsulfonylbenzoic acid in 40 ml of methanol were then added. After stirring for 12 hours at room temperature, the solvent was removed, the residue was taken up in ethyl acetate and the organic phase was washed four times with water. After drying and removal of the solvent by distillation, 3.60 g of 2-chloro-3-ethoxyiminomethyl-4-methylsulfonylbenzoic acid (78% yield) were obtained.

(mp.: 155–160° C.)

alternatively:

Step g') Methyl 2-chloro-3-ethoxyiminomethyl-4-methylsulfonyl-benzoate (compound 3.01)

1.90 g (0.0195 mol) of O-ethylhydroxylamine hydrochloride and 1.35 g (0.0097 mol) of finely powdered potassium carbonate were stirred for 1 hour at room temperature in 60 ml of dry methanol, and 4.90 g (0.0177 mol) of methyl 2-chloro-3-formyl-4-methylsulfonylbenzoate were then added. After stirring for 8 hours at room temperature, the solvent was removed, the residue was taken up in ethyl acetate and the organic phase was washed with water until neutral, dried and concentrated under reduced pressure. 5.00 g of methyl 2-chloro-3-ethoxyiminomethyl-4-methylsulfonylbenzoate were obtained. (Yield 88%).

($^1$H NMR (CDCl$_3$, δ in ppm): 1.34 (t, 3H); 3.29 (s, 3H); 3.98 (s, 3H); 4.26 (q, 2H); 7.91 (d, 1H); 8.10 (d, 1H); 8.38 (s, 1H).)

Step h') 2-Chloro-3-ethoxyiminomethyl-4-methylsulfonylbenzoic acid

A solution of 4.37 g (0.0137 mol) of methyl 2-chloro-3-ethoxyiminomethyl-4-methylsulfonylbenzoate was slowly added dropwise to 7.29 g (0.055 mol) of lithium iodide in 50 ml of dry pyridine. After stirring for 2 hours at reflux, the reaction mixture was cooled and the solvent was removed under reduced pressure. The residue was taken up in water and adjusted to pH=1–2 with dilute hydrochloric acid. The aqueous phase was extracted with ethyl acetate and the combined organic phases were washed with water, dried and concentrated under reduced pressure. 3.70 g of 2-chloro-3-ethoxyiminomethyl-4-methylsulfonylbenzoic acid were obtained. (Yield 89%).

(mp.: 155–160° C.)

Methyl 2-chloro-3-chlorocarbonyl-4-methylsulfonylbenzoate

Step a) Methyl 2-chloro-3-hydroxycarbonyl-4-methylsulfonylbenzoate

At 5° C., 13.8 g (0.11 mol) of sodium hydrogen phosphate monohydrate in 170 ml of water, 49.3 g (0.43 mol) of 30% strength hydrogen peroxide solution and 66.2 g (0.59 mol) of 80% strength aqueous sodium chlorite solution were added in succession to a solution of 115.3 g (0.42 mol) of methyl 2-chloro-3-formyl-4-methylsulfonylbenzoate and 2000 ml of acetonitrile. The reaction solution was then stirred for 1 hour at 5° C. and for 12 hours at room temperature. The pH was then adjusted to 1 using 10% strength hydrochloric acid, and 1500 ml of aqueous 40% strength sodium hydrogen sulfite solution were added. After stirring for 1 hour at room temperature, the aqueous phase was extracted three times with ethyl acetate. The combined organic phases were washed with sodium hydrogen sulfite solution and dried. Removal of the solvent by distillation gave 102.0 g of methyl 2-chloro-3-hydroxycarbonyl-4-methylsulfonylbenzoate.

($^1$H NMR (d$^6$-DMSO, δ in ppm): 3.34 (s, 3H); 3.93 (s, 3H); 8.08 (s, 2H); 14.50 (s, br., 1H).)

Step b) Methyl 2-chloro-3-chlorocarbonyl-4-methylsulfonylbenzoate 2 drops of dimethylformamide and 11.9 g (0.1 mol) of thionyl chloride were added to a solution of 6.0 g (0.021 mol) of methyl 2-chloro-3-hydroxycarbonyl-4-methylsulfonylbenzoate and 50 ml of dry toluene. The solution was heated under reflux for 4 hours. After removal of the solvent under reduced pressure, 6.2 g of methyl 2-chloro-3-chlorocarbonyl-4-methylsulfonylbenzoate were obtained.

($^1$H NMR (CDCl$_3$; δ in ppm): 3.21 (s, 3H); 4.02 (s, 3H); 8.02 (d, 1H); 8.07 (d, 1H).)

2,4-Dichloro-3-(1'-methoxyimino-1'-(methoxy)methyl)benzoyl chloride (compound 3.14)

Step a) 2,4-Dichloro-3-methylacetophenone

At 100° C., 235.0 g (3.0 mol) of acetyl chloride were added dropwise with stirring over a period of 2 hours to a solution of 502.0 g (3.12 mol) of 2,6-dichlorotoluene and 408.0 g (3.06 mol) of aluminum trichloride. After 2 hours of stirring at 100–105° C., the reaction mixture was cooled and poured into 3 l of ice and 1 l of water. The precipitated solid was filtered off with suction and washed with 800 ml of water until neutral. Drying at 40° C. yielded 500.0 g of crude 2,4-dichloro-3-methylacetophenone which was subsequently distilled using high vacuum.

(bp.: 121–128° C. (4 mbar))

Step b) 2,4-Dichloro-3-methylbenzoic acid

At 0–10° C., first 655.2 g (4.1 mol) of bromine and then 203.0 g (1.0 mol) of 2,4-dichloro-3-methyl-acetophenone in 1300 ml of 1,4-dioxane were added dropwise to a solution of 520.0 g (13 mol) of sodium hydroxide in 2600 ml of water. After stirring for 12 hours, the organic phase was separated off, the aqueous phase was admixed with a 30% strength aqueous sodium pyrosulfite solution and the pH was adjusted to 1 using hydrochloric acid. The precipitated solid was filtered off with suction, washed with water and dried at 60° C. under reduced pressure. 197.0 g of 2,4-dichloro-3-methylbenzoic acid were obtained.

(mp.: 173–175° C.)

Step c) Methyl 2,4-dichloro-3-methylbenzoate 60 ml of concentrated sulfuric acid were added dropwise to a solution of 424.0 g (2 mol) of 2,4-dichloro-3-methylbenzoic acid and 1500 ml of methanol. After heating for 5 hours under reflux, the reaction mixture was cooled, concentrated under reduced pressure and then taken up in 1000 ml of methylene chloride. The organic phase was washed with water, then with 5% strength of sodium hydrogen carbonate solution and then again with water, dried and concentrated under reduced pressure. 401.0 g of methyl 2,4-dichloro-3-methylbenzoate were obtained.

(bp: 103–107° C. (1–1.5 mbar))

Step d) Methyl 3-bromomethyl-2,4-dichlorobenzoate 1.0 g of azobisisobutyronitrile was added to a solution of 84.0 g (0.38 mol) of methyl 2,4-dichloro-3-methylbenzoate and 67.6 g (0.38 mol) of N-bromosuccinimide in 380 ml of carbon tetrachloride. After heating for 3.5 hours under reflux, the reaction mixture was cooled and the resulting precipitate was filtered off with suction. The filtrate was concentrated under reduced pressure and the resulting residue was triturated with methyl tert-butyl ether. 108.0 g of methyl 3-bromomethyl-2,4-dichlorobenzoate were obtained.

(mp.: 51–54° C.)

Step e) Methyl 2,4-dichloro-3-formylbenzoate

At reflux, 696.2 g (2.97 mol) of aqueous 50% strength N-methylmorpholine N-oxide solution were added to a solution of 312.0 g (0.99 mol) of methyl 3-bromomethyl-2,4-dichlorobenzoate in 2 l of acetonitrile. After stirring for 48 hours at room temperature, the reaction solution was stirred into 6 l of water. The precipitate was filtered off with suction, washed with water and dried under reduced pressure. 141.3 g of methyl 2,4-dichloro-3-formylbenzoate were obtained.

($^1$H NMR (CDCl$_3$, δ in ppm): 3.98 (s, 3H); 7.47 (d, 1H); 7.84 (d, 1H); 10.48 (s, 1H).)

Step f) Methyl 2,4-dichloro-3-hydroxycarbonylbenzoate

At 5° C., 5.9 g (0.043 mol) of sodium dihydrogen phosphate monohydrate in 70 ml of water, 20.5 g (0.181 mol) of 30% strength hydrogen peroxide solution and 27.3 g (0.241 mol) of 80% strength sodium chlorite solution were added in succession to a solution of 40.0 g (0.172 mol) of methyl 2,4-dichloro-3-formylbenzoate and 500 ml of acetonitrile. The reaction solution was stirred for 1 hour at 5° C. and for 12 hours at room temperature. Subsequently, the pH was adjusted to 1 with 10% strength hydrochloric acid and 500 ml of 40% strength sodium hydrogen sulfite solution were added. After stirring for 1 hour at room temperature, the aqueous phase was extracted three times with ethyl acetate and the combined organic phases were washed with 1.0 l of 10% strength sodium hydrogen sulfite solution and then dried. Removal of the solvent by distillation gave 40.0 g of methyl 2,4-dichloro-3-hydroxycarbonylbenzoate. ($^1$H NMR (d$^6$-DMSO, δ in ppm): 3.90 (s, 3H); 7.69 (d, 1H); 7.89 (d, 1H).)

Step g) Methyl 3-chlorocarbonyl-2,4-dichlorobenzoate 2 drops of dimethylformamide and 11.90 g (0.1 mol) of thionyl chloride were added to a solution of 5.00 g (0.02 mol) of methyl 2,4-dichloro-3-hydroxycarbonylbenzoate and 50 ml of dry toluene. The solution was heated under reflux for 4 hours. Removal of the solvent by distillation gave 5.35 g of methyl 3-chlorocarbonyl-2,4-dichlorobenzoate.

Step h) Methyl 2,4-dichloro-3-methoxyaminocarbonylbenzoate 4.60 g (0.045 mol) of triethylamine and 3.75 g (0.045 mol) of O-methylhydroxylamine hydrochloride were added to a solution of 5.35 g (0.02 mol) of methyl 3-chlorocarbonyl-2,4-dichlorobenzoate and 100 ml of dichloromethane. After stirring for 12 hours at room temperature, the reaction solution was washed with dilute phosphoric acid, dried and concentrated. The residue that was obtained was triturated with diethyl ether. This gave 4.80 g of methyl 2,4-dichloro-3-methoxyaminocarbonylbenzoate.

(mp.: 162–164° C.)

Step i) Methyl 2,4-dichloro-3-(1'-methoxyimino-1'-(methoxy)methyl)benzoate (compound 3.09)

A mixture of 16.0 g (0.058 mol) of methyl 2,4-dichloro-3-methoxyaminocarbonylbenzoate and 10.1 g (0.073 mol) of potassium carbonate in 300 ml of dimethylformamide was stirred at room temperature for 30 minutes. 11.0 g (0.087 mol) of dimethyl sulfate were then added, the mixture was stirred for 12 hours at room temperature, and a further 11.0 g of dimethyl sulfate were added. The reaction mixture was heated to 60° C. for 6 hours, cooled and stirred into 2 l of ice-water. The aqueous phase was then extracted with ethyl acetate, the combined organic phases were dried and the solvent was distilled off under reduced pressure. Silica gel chromatography of the residue (eluent:toluene/ethyl acetate=9/1) afforded 2.0 g of methyl 2,4-dichloro-3-(1'-methoxyimino-1-(methoxy)methyl)benzoate.

($^1$H NMR (CDCl$_3$, δ in ppm): 3.43 (s, 3H); 3.58 (s, 3H); 3.92 (s, 3H); 7.35 (d, 1H); 7.82 (d, 1H).)

Step j) 2,4-Dichloro-3-(1'-methoxyimino-1'-(methoxy)methyl)benzoic acid (compound 3.10)

A solution of 2.20 g (0.008 mol) of methyl 2,4-dichloro-3-(1'-methoxyimino-1l-(methoxy)methyl)benzoate and 3.00 g (0.075 mol) of sodium hydroxide in 50 ml of water was stirred at 80° C. for 2 hours. After cooling, the reaction mixture was stirred into 200 ml of ice-water and adjusted to pH=1 with concentrated hydrochloric acid. The aqueous phase was extracted with ethyl acetate and the combined organic phases were dried and concentrated under reduced pressure. 2.10 g of 2,4-dichloro-3-(1l-methoxyimino-1'-(methoxy)methyl)benzoic acid were obtained.

$^1$H NMR (d$^6$-DMSO, δ in ppm): 3.53 (s, 3H); 3.72 (s, 3H); 7.74 (d, 1H); 7.95 (d, 1H).)

Step k) 2,4-Dichloro-3-(1'-methoxyimino-1-(methoxy)methyl)benzoyl chloride (compound 3.14)

A solution of 2.10 g (0.0076 mol) of 2,4-dichloro-3-(1'-(methoxy)imino-1'-methoxymethyl)benzoic acid and 20.00 g of thionyl chloride in 50 ml of dry toluene was stirred at 80° C. for 2 hours. Removal of the solvent under reduced pressure afforded 2.25 g of 2,4-dichloro-3-(1'-methoxyimino-1'-(methoxy)methyl)benzoyl chloride Methyl 2,4-dichloro-3-propoxyaminocarbonylbenzoate At 30° C., 10.7 g (0.04 mol) of methyl 3-chlorocarbonyl-2,4-dichlorobenzoate in 100 ml of methylene chloride were slowly added dropwise to a solution of 4.50 g (0.04 mol) of O-propylhydroxylamine hydrochloride and 4.05 g (0.04 mol) of triethylamine in 200 ml of methylene chloride. After stirring for 2 hours at room temperature, the reaction mixture was washed with dilute phosphoric acid, dried and concentrated. The resulting residue was chromatographed over silica gel (eluent:toluene/ethyl acetate=9/1). 11.50 g.of methyl 2,4-dichloro-3-propoxyaminocarbonylbenzoate were obtained.

(mp.: 80–81° C.)

Methyl 3-(4-chlorobenzyloxyaminocarbonyl)-2,4-dichlorobenzoate

At about 30° C., 10.70 g (0.04 mol) of methyl 3-chlorocarbonyl-2,4-dichlorobenzoate in 50 ml of methylene chloride were slowly added dropwise to a solution of 7.76 g (0.04 mol) of O-(4-chlorobenzyl)hydroxylamine hydrochloride and 4.05 g (0.04 mol) of triethylamine in 200 ml of methylene chloride. After stirring for 12 hours at room temperature, the reaction mixture was washed with dilute phosphoric acid, dried and concentrated. Trituration of the residue with diethyl ether gave 19.00 g of methyl 3-(4-chlorobenzyloxyaminocarbonyl)-2,4-dichlorobenzoate.

(mp.: 120–121° C.)

3-(1'-Methoxyiminoeth-1'-yl)-2-methyl-4-methylsulfonylbenzoic acid (Compound 3.22)

Step a) 3-(1'-Methoxyiminoeth-1'-yl)-2-methylaniline 50.0 g (0.335 mol) of 3-amino-2-methylacetophenone, 66.3 g (0.838 mol) of pyridine and 42.0 g (0.503 mol) of O-methylhydroxylamine hydrochloride were stirred at room temperature in 400 ml of ethanol. The solvent was removed and the residue was taken up in methylene chloride, washed with water, dried and concentrated. This gave 54.0 g (91% of theory) of 3-(1'-methoxyiminoeth-1'-yl)-2-methylaniline.

Step b) 3-(1'-Methoxyiminoeth-1'-yl)-2-methyl-4-thiocyanatoaniline

At from −20 to −15° C., 50.9 g (0.319 mol) of bromine were added dropwise to 54.0 g (0.303 mol) of 3-(1'-methoxyiminoeth-1'-yl)-2-methylaniline, 49.3 g (0.479 mol) of sodium bromide and 77.5 g (0.956 mol) of sodium thiocyanate in 300 ml of methanol. The mixture was stirred at this temperature for 30 minutes, the insoluble components were filtered off with suction, the filtrate was admixed with ethyl acetate and the pH was adjusted to 8 using aqueous sodium bicarbonate solution. The organic phase was separated off and the remaining aqueous phase was extracted repeatedly with ethyl acetate. The combined organic phases were then washed with water, dried and concentrated. This gave 67.3 g (95% of theory) of 3-(1'-methoxyiminoeth-1'-yl)-2-methyl-4-thiocyanatoaniline.

Step c) 3-(1'-Methoxyiminoeth-1'-yl)-2-methyl-4-methylthioaniline

At from 20 to 30° C., 67.3 g (0.286 mol) of 3-(1-methoxyiminoeth-1'-yl)-2-methyl-4-thiocyanatoaniline in 600 ml of methanol were added dropwise to 40.4 g (0.315 mol) of sodium sulfide in 200 ml of water. The mixture was stirred at room temperature for 3 hours and 45.1 g (0.318 mol) of methyl iodide in 200 ml of methanol were then added, again at from 20 to 30° C. The mixture was subsequently stirred at room temperature for 12 hours, the solvent was removed and the residue was taken up in water and extracted repeatedly with ethyl acetate. The combined organic phases were then washed with water, dried and concentrated and the resulting residue was digested with n-hexane/methyl tert-butyl ether. This gave 43.2 g (67% of theory) of 3-(1'-methoxyiminoeth-1'-yl)-2-methyl-4-methylthioaniline.

(mp.: 83–89° C.)

Step d) 6-Bromo-2-(1'-methoxyiminoeth-1'-yl)-3-methylthiotoluene

At room temperature, 9.23 g of 47% strength hydrobromic acid were added dropwise to 3.00 g (13.4 mmol) of 3-(1'-methoxyiminoeth-1'-yl)-2-methyl-4-methylthioaniline in 13.40 g of glacial acetic acid. 9.23 g of water were subsequently added, the mixture was stirred at room temperature for 10 minutes and 0.92 g (13.4 mmol) of sodium nitrite in 1.9 ml of water was added at from −5 to 0° C. At 0° C., the resulting reaction mixture was then added dropwise to 1.92 g (13.4 mmol) of copper(I) bromide in 6 ml of 47% strength hydrobromic acid. The mixture was stirred at room temperature for 12 hours, then poured into ice-water and extracted with methylene chloride. The organic phase was then washed with sodium sulfite solution and water and dried and the solvent was removed. This gave 2.50 g (65% of theory) of 6-bromo-2-(1'-methoxyiminoeth-1'-yl)-3-methylthiotoluene.

Step e) 6-Bromo-2-(1'-methoxyiminoeth-1'-yl)-3-methylsulfonyltoluene

Over a period of 96 hours, a total of 7.0 g (34.80 mmol) of m-chloroperbenzoic acid were added a little at a time to 2.5 g (8.71 mmol) of 6-bromo-2-(1'-methoxyimino-1'-yl)-3-methylthiotoluene [sic] in 50 ml of methylene chloride. The solvent was removed and the residue was taken up in an organic solvent, washed a [sic] sodium carbonate solution, sodium sulfite solution and water, dried and concentrated. The residue was then chromatographed over silica gel (eluent:toluene/ethyl acetate). This gave 0.8 g (29% of theory) of 6-bromo-2-(1'-methoxyiminoeth-1'-yl)-3-methylsulfonyltoluene.

Step f) 3-(1'-Methoxyiminoeth-1'-yl)-2-methyl-4-methylsulfonylbenzoic acid 0.77 g (2.41 mmol) of 6-bromo-2-(1'-methoxyiminoeth-1'-yl)-3-methylsulfonyltoluene, 0.03 g (0.1 mmol) of palladium acetate, 0.14 g (0.49 mmol) of tricyclohexylphosphine, 0.10 g (2.4 mmol) of lithium chloride and 0.49 g (4.81 mmol) of triethylamine were suspended in 37.5 ml of toluene and 17.5 ml of water and gassed at 140° C. and a pressure of 20 bar for 36 hours. After cooling, the insoluble particles were then separated off, the organic phase was extracted with water (which had been admixed with 1 ml of triethylamine) and the resulting aqueous phase was adjusted to pH=1 using hydrochloric acid and extracted with methylene chloride. This organic phase was dried and concentrated. This gave 0.62 g (90% of theory) of 3-(1'-methoxyiminoeth-1'-yl)-2-methyl-4-methylsulfonylbenzoic acid.

In addition to the compounds described above, further benzoic acid derivatives of the formula IIIa which were prepared or are preparable in a similar manner are listed in Table 3 below.

TABLE 3

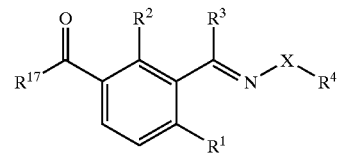

IIIa (≙ III where $R^1$ is attached in position 4, and $R^2$ is attached in position 2)

| No. | X | $R^1$ | $R^2$ | $R^3$ | $R^4$ | $R^{17}$ | mp. [° C.]<br>$^1$H NMR [ppm] |
|---|---|---|---|---|---|---|---|
| 3.01 | O | $SO_2CH_3$ | Cl | H | $C_2H_5$ | $OCH_3$ | 1.34(t, 3H); 3.29(s, 3H); 3.98(s, 3H); 4.26(q, 2H); 7.91(d, 1H); 8.10(d, 1H); 8.38(s, 1H) |
| 3.02 | O | Cl | Cl | H | $CH_3$ | $OCH_3$ | 55–57 |
| 3.03 | O | Cl | Cl | H | $C_2H_5$ | $OCH_3$ | 1.35(t, 3H); 3.93(s, 3H); 4.27(q, 2H); 7.42(d, 1H); 7.69(d, 1H); 8.24(s, 1H) |
| 3.04 | O | $SO_2CH_3$ | Cl | H | $C_2H_5$ | OH | 155–160 |
| 3.05 | O | Cl | Cl | H | $C_2H_5$ | OH | 120–123 |
| 3.06 | O | Cl | Cl | H | $CH_3$ | OH | 168–169 |
| 3.07 | O | Cl | Cl | H | $CH_2C{\equiv}CH$ | OH | 155–160 |
| 3.08 | O | Cl | Cl | $OC_2H_5$ | n-$C_3H_7$ | OH | 105–106 |
| 3.09 | O | Cl | Cl | $OCH_3$ | $CH_3$ | $OCH_3$ | 3.43(s, 3H); 3.58(s, 3H); 3.92(s, 3H); 7.35(d, 1H); 7.82(d, 1H) |
| 3.10 | O | Cl | Cl | $OCH_3$ | $CH_3$ | OH | 3.53(s, 3H); 3.72(s, 3H); 7.74(d, 1H); 7.95(d, 1H) |
| 3.11 | O | Cl | Cl | $OCH_3$ | $CH_2$-4-Cl—$C_6H_4$ | OH | 3.55(s, 3H); 5.08(s, 2H); 7.18–7.30(m, 2H); 7.36(d, 1H); 8.03(d, 1H); 9.14(s, br., 1H) |
| 3.12 | O | Cl | Cl | $OCH_3$ | n-$C_3H_7$ | $OCH_3$ | 47–48 |
| 3.13 | O | Cl | Cl | $OC_2H_5$ | n-$C_3H_7$ | $OCH_3$ | 48–50 |

TABLE 3-continued

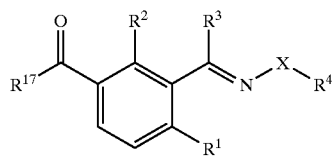

IIIa (≙ III where $R^1$ is attached in position 4, and $R^2$ is attached in position 2)

| No. | X | $R^1$ | $R^2$ | $R^3$ | $R^4$ | $R^{17}$ | mp. [° C.] $^1$H NMR [ppm] |
|---|---|---|---|---|---|---|---|
| 3.14 | O | Cl | Cl | $OCH_3$ | $CH_3$ | Cl | |
| 3.15 | O | $SO_2CH_3$ | Cl | H | $CH_2C_6H_5$ | $OCH_3$ | 95–100 |
| 3.16 | O | $SO_2CH_3$ | Cl | H | $CH_2C_6H_5$ | OH | 115–120 |
| 3.17 | O | $SO_2CH_3$ | Cl | H | $CH_2$-3-thienyl | $OCH_3$ | 90–95 |
| 3.18 | O | $SO_2CH_3$ | Cl | H | $CH_3$ | $OCH_3$ | 95–100 |
| 3.19 | O | $SO_2CH_3$ | Cl | H | $CH_3$ | OH | 180–185 |
| 3.20 | O | $SO_2CH_3$ | Cl | H | $CH_2$-3-thienyl | OH | 95–100 |
| 3.21 | O | $SO_2CH_3$ | Cl | $CH_3$ | $CH_3$ | OH | |
| 3.22 | O | $SO_2CH_3$ | $CH_3$ | $CH_3$ | $CH_3$ | OH | oil |

The 2-benzoylcyclohexane-1,3-diones of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula I, or compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa , Phaseolus lunatus, Phaseolus vulgaris, Picea abies, Pinus* spec., *Pisum sativum, Prunus avium, Prunus persica, Pyrus communis, Ribes sylestre* [sic], *Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The compounds of the formula I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee the finest possible distribution of the active ingredients according to the invention.

The herbicidal compositions comprise a herbicidally active amount of at least one compound of the formula I or an agriculturally useful salt of I and auxiliaries conventionally used in the formulation of crop protection agents.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates [sic], either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ether, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound. The active compounds are employed in a purity of from 90% to 100%, preferably 95% to 100% (according to NMR spectrum).

The formulation examples which follow illustrate the preparation of the compounds I according to the invention:

I. 20 parts by weight of the compound No. 2.01 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 2.03 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 2.05 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 2.07 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 2.10 are mixed with 97 parts by weight of finely divided kaolin. This gives a dust which comprises 3% by weight of active compound.

VI. 20 parts by weight of the active compound No. 2.14 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 2.06 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 2.09 is dissolved in a mixture [lacuna] of 80 parts by weight of cyclohexanone and 20 parts by weight of Wettol® EM 31 (nonionic emulsifier based on ethoxylated castor oil). This gives a stable emulsion concentrate.

The active compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active ingredients reach the leaves of undesirable plants growing underneath, or the bare soil surface (post-directed, lay-by).

To widen the spectrum of action and to achieve synergistic effects, the compounds of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, aryl-/hetaryl-oxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivates, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4, 5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The rates of application of active compound I are from 0.001 to 3.0, preferably 0.01 to 1.0, kg/ha of active substance (a.s.), depending on the control target, the season, the target plants and the growth stage Use Examples The herbicidal activity of the 2-benzoylcyclohexane-1,3-diones of the formula I was demonstrated by the following greenhouse experiments:

The culture containers used were plastic flowerpots containing loamy soil with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover causes [sic] uniform germination of the test plants, unless this was adversely affected by the active ingredients.

For the post-emergence treatment, the test plants were first grown to a plant height of 3 to 15 cm, depending on the plant habit, and only then treated with the active compounds which had been suspended or emulsified in water. The test plants for this purpose were either sown directly and grown in the same containers, or they were first grown separately as seedlings and transplanted into the test containers a few days prior to treatment. The rate of application for the post-emergence treatment was 0.125.or 0.0625 kg/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
| --- | --- |
| Chenopodium album | lambsquarters (goosefoot) |
| Echinochloa crus galli | barnyardgrass |
| Sinapis alba | white mustard |
| Zea mays | maize |

At application rates of 0.125 or 0.0625 kg/ha (of a.s.), the compound 2.07 (Table 2) exhibited a very good activity against the abovementioned mono- and dicotyledonous harmful plants when applied post-emergence and was well tolerated in maize.

We claim:
1. 2-Benzoylcyclohexane-1,3-diones of the formula I

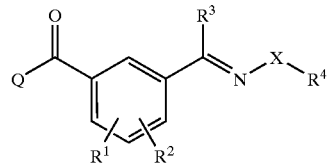

where:
  $R^1$ and $R^2$ are each hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$, —$OCOR^6$, —$OSO_2R^6$, —SH, —S(O)$_n$$R^7$, —$SO_2OR^5$, —$SO_2NR^5R^8$, —$NR^8SO_2R^6$ or —$NR^8COR^6$;
  $R^3$ is hydrogen, cyano, $C_1$–$C_6$-alkyl, $C_1$–$C_6$-haloalkyl, —$OR^7$, —$SR^7$ or —$NR^7R^{10}$;
  $R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, where the alkyl, cycloalkyl, alkenyl, cycloalkenyl and alkynyl radicals mentioned and $R^9$ of the radicals —$COR^9$, —$CO_2R^9$, —$COSR^9$ and —$CONR^8R^9$ may be partially or fully halogenated and/or carry one to three of the following groups:
  hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;
  X is oxygen or $NR^8$;
  n is 0, 1 or 2;
  $R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
  $R^6$ is $C_1$–$C_6$-alkyl or $C_1$–$C_6$-haloalkyl;
  $R^7$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
  $R^8$ is hydrogen or $C_1$–$C_6$-alkyl;
  $R^9$ is $C_1$–$C_6$-alkyl, $C_3$–$C_6$-alkenyl, $C_3$–$C_6$-alkynyl, phenyl or benzyl;
  $R^{10}$ is $C_1$–$C_6$-alkyl, $C_1$–$C_6$-haloalkyl, $C_3$–$C_6$-alkenyl or $C_3$–$C_6$-alkynyl;
  Q is a cyclohexane-1,3-dione ring attached in position 2 with or without substitution;

2. 2-Benzoylcyclohexane-1,3-diones of the formula I as claimed in claim 1 in which Q is a cyclohexane-1,3-dione ring of the formula II

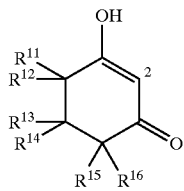

attached in position 2 where $R^{11}$, $R^{12}$, $R^{14}$ and $R^{16}$ are each hydrogen or $C_1$–$C_4$-alkyl;

$R^{13}$ is hydrogen, $C_1$–$C_4$-alkyl or $C_3$–$C_4$-cycloalkyl, where the last two groups may carry one to three of the following substituents:
halogen, $C_1$–$C_4$-alkylthio or $C_1$–$C_4$-alkoxy; or
is tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the last 6 radicals mentioned may be substituted by one to three $C_1$–$C_4$-alkyl radicals;

$R^{15}$ is hydrogen, $C_1$–$C_4$-alkyl or $C_1$–$C_6$-alkoxycarbonyl; or $R^{13}$ and $R^{16}$ together form a π-bond or a three- to six-membered carbocyclic ring; or the $CR^{13}R^{14}$ unit is replaced by C=O.

3. 2-Benzoylcyclohexane-1,3-diones of the formula I as claimed in claim 1, where $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;

$R^2$ is hydrogen or one of the radicals mentioned above under $R^1$.

4. 2-Benzoylcyclohexane-1,3-diones of the formula Ia

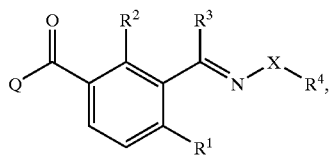

where the variables $R^1$ to $R^4$, X and Q are each as defined under claim 1.

5. A process for preparing 2-benzoylcyclohexane-1,3-diones of the formula I as claimed in claim 1, which comprises acylating an unsubstituted or substituted cyclohexane-1,3-dione Q with an activated carboxylic acid IIIα or with a carboxylic acid IIIβ,

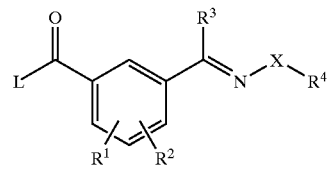

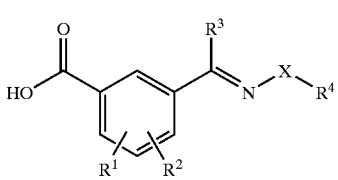

where the variables $R^1$ to $R^4$ and X are each as defined under claim 1 and L is a nucleophilically displaceable leaving group, and rearranging the acylation product in the presence or absence of a catalyst to the compounds I.

6. A composition comprising a herbicidally active amount of at least one compound of the formula I or an agriculturally useful salt of I as claimed in claim 1, and auxiliaries conventionally used in the formulation of crop protection agents.

7. A process for preparing herbicidally active compositions as claimed in claim 6, which comprises mixing the herbicidally active amount of the at least one compound of formula I or the agriculturally useful salt and auxiliaries conventionally used in the formulation of crop protection agents.

8. A method for controlling undesirable vegetation, which comprises allowing a herbicidally active amount of at least one compound of the formula I or an agriculturally useful salt of I as claimed in claim 1 to act on plants, their habitat and/or on seeds.

9. A benzoic acid compound of formula IIIa,

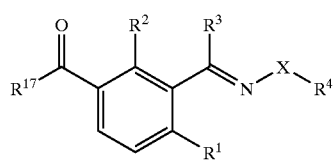

wherein $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl or —$S(O)_nR^7$;

$R^2$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;

$R^3$ is hydrogen, cyano, $C_1$–$C_6$-alkyl, $C_1$–$C_6$-haloalkyl, —$OR^7$, —$SR^7$ or —$NR^7R^{10}$;

$R^4$ is $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, where the alkyl, cycloalkyl, alkenyl, cycloalkenyl and alkynyl radicals mentioned and $R^9$ of the radicals —$COR^9$, —$CO_2R^9$, —$COSR^9$ and —$CONR^8R^9$ may be partially or fully halogenated and/or carry one to three of the following groups:
hydroxyl, mercapto, amino, cyano, $R^{10}$, —$OR^{10}$, —$SR^{10}$, —$NR^8R^{10}$, =$NOR^{10}$, —$OCOR^{10}$, —SCOR$^{10}$, —NR$^8$COR$^{10}$, —CO$_2$R$^{10}$, —COSR$^{10}$, —CONR$^8$R$^{10}$, C$_1$–C$_4$-alkyliminooxy, C$_1$–C$_4$-alkoxyamino, C$_1$–C$_4$-alkylcarbonyl, C$_1$–C$_4$-alkoxy-C$_2$–C$_6$-alkoxycarbonyl, C$_1$–C$_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

X is oxygen or NR$^8$;
  n is 0, 1 or 2;
  R$^5$ is hydrogen, C$_1$–C$_6$-alkyl, C$_1$–C$_6$-haloalkyl, C$_1$–C$_6$-alkoxy-C$_2$–C$_6$-alkyl, C$_3$–C$_6$-alkenyl or C$_3$–C$_6$-alkynyl;
  R$^7$ is C$_1$–C$_6$-alkyl, C$_1$–C$_6$-haloalkyl, C$_1$–C$_6$-alkoxy-C$_2$–C$_6$-alkyl, C$_3$–C$_6$-alkenyl or C$_3$–C$_6$-alkynyl;
  R$^8$ is hydrogen or C$_1$–C$_6$-alkyl;
  R$^9$ is C$_1$–C$_6$-alkyl, C$_3$–C$_6$-alkenyl, C$_3$–C$_6$-alkynyl, phenyl or benzyl;
  R$^{10}$ is C$_1$–C$_6$-alkyl, C$_1$–C$_6$-haloalkyl, C$_3$–C$_6$-alkenyl or C$_3$–C$_6$-alkynyl;
  R$^{17}$ is hydroxyl or a radical that can be removed by hydrolysis.

10. The compound of formula IIIa as claimed in claim 9, where R$^{17}$ is halogen, hydroxyl or C$_1$–C$_6$-alkoxy.

* * * * *

UNITED STATES PATENT AND TRADEMARK OFFICE
CERTIFICATE OF CORRECTION

PATENT NO.     : 6,576,596 B1
DATED          : June 10, 2003
INVENTOR(S)    : Regina L. Hill et al.

It is certified that error appears in the above-identified patent and that said Letters Patent is hereby corrected as shown below:

<u>Title page,</u>
Item [87], the PCT Pub. Date should be -- July 9, 1998 --.
Item [57] ABSTRACT,
Lines 4 and 5, after formula I, the line break is inappropriate, i.e., "-S(O)$_n$R$^7$" should all be on one line.

<u>Column 42,</u>
Line 64, the "R$^{10}$" should be brought left to line up with the other substituents.

<u>Column 46,</u>
Line 6, the "R$^{10}$" should be brought left to line up with the other substituents.

Signed and Sealed this

Ninth Day of September, 2003

JAMES E. ROGAN
*Director of the United States Patent and Trademark Office*